(12) United States Patent
Okamura et al.

(10) Patent No.: US 6,288,070 B1
(45) Date of Patent: Sep. 11, 2001

(54) TRIAZOLOPURINE DERIVATIVES, MEDICINAL COMPOSITION CONTAINING THE DERIVATIVES, ADENOSINE A3 RECEPTOR COMPATIBILIZING AGENT, AND ASTHMATIC REMEDY

(75) Inventors: Takashi Okamura; Yasuhisa Kurogi; Hiroshi Nishikawa, all of Tokushima (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 09/647,613

(22) PCT Filed: Mar. 26, 1999

(86) PCT No.: PCT/JP99/01592

§ 371 Date: Oct. 3, 2000

§ 102(e) Date: Oct. 3, 2000

(87) PCT Pub. No.: WO99/51606

PCT Pub. Date: Oct. 14, 1999

(30) Foreign Application Priority Data

Apr. 3, 1998 (JP) .................................................. 10-091367
Oct. 12, 1998 (JP) .................................................. 10-289194

(51) Int. Cl.[7] .......................... A01N 43/54; A61K 31/505; C07D 239/00; C07D 487/00
(52) U.S. Cl. ............................ 514/267; 544/251; 544/252
(58) Field of Search ......................... 514/267; 544/251, 544/252

(56) References Cited

U.S. PATENT DOCUMENTS 5,935,964  *  8/1999  Baraldi et al. ........................ 514/267

OTHER PUBLICATIONS

Franco Gatta et al, "Synthesis of 2,8–Disubstituted 1,2, 4–Triazolo[5,1–i]purines", Journal of Heterocyclic Chemistry, 1994, vol. 31, pp. 1171–1176.

Shoji Asano et al, Reactions of 9–Substituted 1–Aminoadenines With Nucleophiles and Syntheses of 3–Substituted 3H–Imidazo[4,5–e]P1,2,4]Triazolo[1,5–c][1,2,3]Triazines, Nucleosides & Nucleotides, 1994, vol. 13, No. 6–7, pp. 1453–1465.

G.F. Huang et al, "Studies on Chemical Alterations of Nucleic Acids and Their Components–IX", Tetrahedron, 1975, vol. 31, pp. 1363–1367.

* cited by examiner

Primary Examiner—Mukund J. Shah
Assistant Examiner—Tamthom N. Truong
(74) Attorney, Agent, or Firm—Sughrue, Mion, Zinn, Macpeak & Seas, PLLC

(57) ABSTRACT

Disclosed is a triazolopurine derivative represented by the general formula:

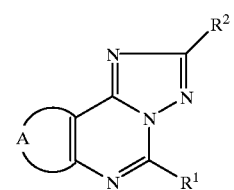

(1)

wherein $R^1$ and $R^2$ represent the same groups as those described in the specification; and A represents a group:

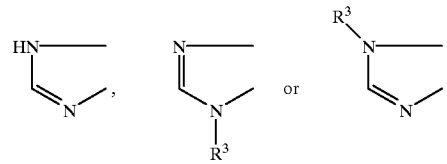

wherein $R^3$ represents the same groups as those described in the specification. This compound is incorporated in a pharmaceutical composition because of its affinity to an adenosine A3 receptor, and is used as an adenosine A3 receptor antagonist or a remedy for asthma.

10 Claims, No Drawings

TRIAZOLOPURINE DERIVATIVES, MEDICINAL COMPOSITION CONTAINING THE DERIVATIVES, ADENOSINE A3 RECEPTOR COMPATIBILIZING AGENT, AND ASTHMATIC REMEDY

TECHNICAL ART

The present invention relates to a novel triazolopurine derivative which exhibits an adenosine A3 receptor affinity, a pharmaceutical composition containing the derivative, an adenosine A3 receptor ligand, and a remedy for asthma.

BACKGROUND ART

J. Heterocyclic Chem., 31, 1171 (1994) discloses that 2-aryl-8-fluorobenzyl-1,2,4-triazolo[5,1-i]purine is useful as an adenosine A2 receptor ligand.

An object of the present invention is to provide a novel compound having an affinity to an adenosine A3 receptor.

DISCLOSURE OF THE INVENTION

The triazolopurine derivative of the present invention is represented by the general formula (1):

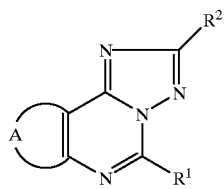

(1)

wherein $R^1$ represents an alkyl group, or a phenyl group which is optionally substituted with a lower alkyl group; $R^2$ represents a pyridyl group, a furyl group, a thienyl group, a lower alkyl group, a phenyl lower alkyl group which optionally has 1 to 3 lower alkoxy groups as a substituent, a styryl group which optionally has 1 to 3 lower alkoxy groups as a substituent, a naphthyl group which optionally has a hydroxy groups as a substituent, or a phenyl group which optionally has 1 to 3 groups selected from lower alkyl group, lower alkoxy group, nitro group, hydroxyl group, amino group, N-lower alkylamino group, N,N-di lower alkylamino group, N-phenyl lower alkylamino group, N,N-bisphenyl lower alkylamino group, phenyl group, phenoxy group, phenyl lower alkoxy group, halogen-substituted lower alkyl group, halogen-substituted lower alkoxy group, di lower alkylphosphorylmethyl group, lower alkylthio group, lower alkoxy lower alkyl group, phenyl lower alkoxy lower alkyl group and halogen atom as a substituent; and A represents a group:

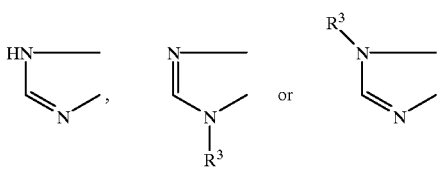

wherein $R^3$ represents a lower alkyl group or a phenyl lower alkyl group.

The triazolopurine derivative of the present invention is a novel compound which has never been described in reference documents.

In the present invention, a triazolopurine derivative wherein A is a group:

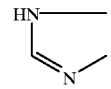

is particularly preferable. In that case, $R^2$ is preferably a pyridyl group, a furyl group, a styryl group, a naphthyl group which optionally has a hydroxyl group as a substituent, a phenyl group which optionally has a group selected from lower alkyl group, N-lower alkylamino group, N,N-di lower alkylamino group, N-phenyl lower alkylamino group, N,N-bisphenyl lower alkylamino group, phenyl group, phenoxy group, phenyl lower alkoxy group, halogen-substituted lower alkyl group, halogen-substituted lower alkoxy group, di lower alkylphosphorylmethyl group, lower alkylthio group, hydroxyl group and halogen atom as a substituent, a phenyl group substituted with a hydroxyl group and a halogen atom, or a phenyl group having 1 to 3 lower alkoxy groups as a substituent.

Particularly preferable compound is a compound selected from the group of the following compounds (a), (b) and (c):

(a) compound wherein $R^1$ is an alkyl group or a lower alkyl-substituted phenyl group and $R^2$ is a phenyl group, (b) compound wherein $R^1$ is a n-butyl group and $R^2$ is a pyridyl group, a furyl group, a styryl group, a naphthyl group which optionally has a hydroxy groups as a substituent, a phenyl group which optionally has a group selected from lower alkyl group, N-lower alkylamino group, N,N-di lower alkylamino group, N-phenyl lower alkylamino group, N,N-bisphenyl lower alkylamino group, phenyl group, phenoxy group, phenyl lower alkoxy group, halogen-substituted lower alkyl group, halogen-substituted lower alkoxy group, di lower alkylphosphorylmethyl group, lower alkylthio group, hydroxyl group and halogen atom as a substituent, a phenyl group substituted with a hydroxyl group and a halogen atom, or a phenyl group having 1 to 3 lower alkoxy groups as a substituent, and (c) compound wherein $R^1$ is a phenyl group and $R^2$ is a phenyl group having 3 lower alkoxy groups.

More preferable compound is a compound selected from the group of the following compounds (i) and (ii):

(i) compound wherein $R^1$ is a lower alkyl group and $R^2$ is a phenyl group, and (ii) compound wherein $R^1$ is a n-butyl group and $R^2$ is a naphthyl group which optionally has a hydroxy group as a substituent, a phenyl group which optionally has a group selected from lower alkyl group, N,N-di lower alkylamino group, N-phenyl lower alkylamino group, phenyl group, phenoxy group, phenyl lower alkoxy group, halogen-substituted lower alkyl group, halogen-substituted lower alkoxy group, di lower alkylphosphorylmethyl group, lower alkylthio group and halogen atom as a substituent, a phenyl group substituted with a hydroxyl group and a halogen atom, or a phenyl group having 1 to 3 lower alkoxy groups as a substituent.

The compound of the present invention is preferably a compound selected from 5-n-butyl-8-(3,4,5-trimethoxyphenyl)-1H-1,2,4-triazolo[5,1-i]purine, 5-n-butyl-8-(4-chlorophenyl)-1H-1,2,4-triazolo[5,1-i]purine, 5-n-butyl-8-(4-methoxyphenyl)-1H-1,2,4-triazolo[5,1-i]purine, 5-n-butyl-8-[4-(N,N-dimethylamino)phenyl]-1H-1, 2,4-triazolo[5,1-i]purine, 5-n-butyl-8-(4-propoxyphenyl)-1H-1,2,4-triazolo[5,1-i]purine, 5-n-butyl-8-(4-ethoxyphenyl)-1H-1,2,4-triazolo[5,1-i]purine, 8-(4-biphenylyl)-5-n-butyl-1H-1,2,4-triazolo[5,1-i]purine, 5-n-butyl-8-(4-trifluoromethylphenyl)-1H-1,2,4-triazolo[5,1-i]purine and 5-n-pentyl-8-phenyl-1H-1,2,4-triazolo[5,1-i]purine, and is particularly preferably a compound selected from 5-n-butyl-8-(4-methoxyphenyl)-1H-1,2,4-triazolo[5,1-i]purine, 5-n-butyl-8-(3,4,5-trimethoxyphenyl)-1H-1,2,4-triazolo[5,1-i]purine and 8-(4-biphenylyl)-5-n-butyl-1H-1,2,4-triazolo[5,1-i]purine.

It is expected that the triazolopurine derivative of the present invention is applied to antihypertensive, antiallergic agent, anti-inflammatory agent, remedy for ischemic heart disease, remedy for leukemia, antipruritic, expectorant, cough medicine, remedy for asthma, and analgesic as a compound capable of binding with an adenosine A3 receptor because of its excellent affinity to an adenosine A3 receptor.

Accordingly, the present invention also provides a pharmaceutical composition comprising the triazolopurine derivative described above and a pharmaceutically acceptable carrier.

Specifically, the present invention provides an adenosine A3 receptor ligand comprising the triazolopurine derivative described above as an active ingredient, and a remedy for asthma, comprising triazolopurine derivative as an active ingredient.

BEST MODE FOR CARRYING OUT THE INVENTION

In the present invention, the lower alkyl group includes, for example, straight-chain or branched lower alkyl groups having 1 to 6 carbon atoms, such as methyl, ethyl, propyl, butyl, isobutyl, tert-butyl, pentyl, and hexyl.

The alkyl group includes, for example, alkyl groups having 7 to 8 carbon atoms, such as heptyl and octyl, in addition to the lower alkyl groups described above.

The lower alkoxy group includes, for example, straight-chain or branched lower alkoxy groups having 1 to 6 carbon atoms, such as methoxy, ethoxy, propoxy, butoxy, tert-butoxy, pentyloxy, and hexyloxy.

The halogen atom includes fluorine, chlorine, bromine, or iodine.

The pyridyl group includes 2-pyridyl, 3-pyridyl and 4-pyridyl.

The furyl group includes 2-furyl and 3-furyl.

The thienyl group includes 2-thienyl group and 3-thienyl group.

The naphthyl group which optionally has a hydroxyl group as a substituent includes, for example, 1-naphthyl, 2-naphthyl, 1-hydroxy-2-naphthyl, 3-hydroxy-2-naphthyl, 4-hydroxy-2-naphthyl, 5-hydroxy-2-naphthyl, 6-hydroxy-2-naphthyl, 7-hydroxy-2-naphthyl, 8-hydroxy-2-naphthyl, 2-hydroxy-1-naphthyl, 3-hydroxy-1-naphthyl, 4-hydroxy-1-naphthyl, 5-hydroxy-1-naphthyl, 6-hydroxy-1-naphthyl, 7-hydroxy-1-naphthyl, and 8-hydroxy-1-naphthyl.

The phenyl which optionally has a group selected from lower alkyl group, lower alkoxy group, nitro group, hydroxyl group, amino group, N-lower alkylamino group, N,N-di lower alkylamino group, N-phenyl lower alkylamino group, N,N-bisphenyl lower alkylamino group, phenyl group, phenoxy group, phenyl lower alkoxy group, halogen-substituted lower alkyl group, halogen-substituted lower alkoxy group, di lower alkylphosphorylmethyl group, lower alkylthio group, lower alkoxy lower alkyl group, phenyl lower alkoxy lower alkyl group and halogen atom as a substituent includes, for example, phenyl groups which optionally have 1 to 3 substituents, such as 2-methylphenyl, 3-methylphenyl, 4-methylphenyl, 4-ethylphenyl, 4-propylphenyl, 4-isopropylphenyl, 4-butylphenyl, 4-t-butylphenyl, 4-pentylphenyl, 4-hexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,4-diethylphenyl, 3,4-dipropylphenyl, 3,4-dibutylphenyl, 3,4-dipentylphenyl, 3,4-dihexylphenyl, 3,4,5-trimethylphenyl, 2,3,4-trimethylphenyl, 2,3,5-trimethylphenyl, 2,3,6-trimethylphenyl, 2,4,6-trimethylphenyl, 2,4,5-trimethylphenyl, 3,4,5-triethylphenyl, 3,4,5-tripropylphenyl, 3,4,5-tributylphenyl, 3,4,5-tripentylphenyl, 3,4,5-trihexylphenyl, 2-methoxyphenyl, 3-methoxyphenyl, 4-methoxyphenyl, 4-ethoxyphenyl, 4-propoxyphenyl, 4-butoxyphenyl, 4-pentyloxyphenyl, 4-hexyloxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,4-diethoxyphenyl, 3,4-dipropoxyphenyl, 3,4-dibutoxyphenyl, 3,4-dipentyloxyphenyl, 3,4-dihexyloxyphenyl, 3,4,5-trimethoxyphenyl, 2,3,4-trimethoxyphenyl, 2,3,5-trimethoxyphenyl, 2,3,6-trimethoxyphenyl, 2,4,6-trimethoxyphenyl, 2,4,5-trimethoxyphenyl, 3,4,5-triethoxyphenyl, 3,4,5-tripropoxyphenyl, 3,4,5-tributoxyphenyl, 3,4,5-tripentyloxyphenyl, 3,4,5-trihexyloxyphenyl, 2-hydroxyphenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxyphenyl, 3,5-dihydroxyphenyl, 3,4,5-trihydroxyphenyl, 2,3,4-trihydroxyphenyl, 2,3,5-trihydroxyphenyl, 2,3,6-trihydroxyphenyl, 2,4,6-trihydroxyphenyl, 2,4,5-trihydroxyphenyl, 2-nitrophenyl, 3-nitrophenyl, 4-nitrophenyl, 2,3-dinitrophenyl, 2,4-dinitrophenyl, 2,5-dinitrophenyl, 2,6-dinitrophenyl, 3,4-dinitrophenyl, 3,5-dinitrophenyl, 3,4,5-trinitrophenyl, 2,3,4-trinitrophenyl, 2,3,5-trinitrophenyl, 2,3,6-trinitrophenyl, 2,4,6-trinitrophenyl, 2,4,5-trinitrophenyl, 2-aminophenyl, 3-aminophenyl, 4-aminophenyl, 3,4-diaminophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-fluorophenyl, 3-fluorophenyl, 4-fluorophenyl, 2,4-dichlorophenyl, 2,3-dichlorophenyl, 3,5-dichlorophenyl, 3,4-dichlorophenyl, 2,5-dichlorophenyl, 2,6-dichlorophenyl, 2,4-difluorophenyl, 2,4-dibromophenyl, 2,4-diiodorophenyl, 3,4,5-trichlorophenyl, 2,4,6-trichlorophenyl, 4-methoxy-3-methylphenyl, 4-methoxy-2-methylphenyl, 3-methoxy-2-methylphenyl, 4-methoxy-3,5-dimethylphenyl, 4-hydroxy-3-methylphenyl, 4-hydroxy-2-methylphenyl, 3-hydroxy-2-methylphenyl, 2-hydroxy-4-methylphenyl, 2-hydroxy-4-methoxyphenyl, 4-hydroxy-3,5-dimethylphenyl, 3,5-di-t-butyl-4-hydroxyphenyl, 4-hydroxy-3,5-dimethoxyphenyl, 3,5-dihydroxy-4-methoxyphenyl, 4-chloro-3-methoxyphenyl, 3-chloro-4-methoxyphenyl, 4-chloro-2-hydroxyphenyl, 4-chloro-3-hydroxyphenyl, 4-chloro-3-methylphenyl, 3-chloro-4-methylphenyl, 4-chloro-3,5-dimethoxyphenyl, 4-chloro-3,5-dimethylphenyl, 4-(N-methylamino)phenyl, 4-(N-ethylamino)phenyl, 4-(N-propylamino)phenyl, 4-(N-butylamino)phenyl, 4-(N-pentylamino)phenyl, 4-(N-hexylamino)phenyl, 3-(N-methylamino)phenyl, 2-(N-methylamino)phenyl, 4-(N,N-dimethylamino)phenyl, 4-(N,N-diethylamino)phenyl, 4-(N,N-dipropylamino)phenyl, 4-(N,N-dibutylamino)phenyl, 4-(N,N-dipentylamino)phenyl, 4-(N,N-dihexylamino) phenyl, 3-(N,N-dimethylamino)phenyl, 2-(N,N-dimethylamino)phenyl, 4-(N-benzylamino)phenyl, 4-[(N-(2-phenylethyl)amino]phenyl, 4-[(N-(3-phenylpropyl)amino]phenyl, 4-[(N-(4-phenylbutyl)amino]phenyl, 4-[(N-(5-phenylpentyl)amino]phenyl, 4-[(N-(6-phenylhexyl)amino]phenyl, 3-(N-benzylamino)phenyl, 2-(N-benzylamino)phenyl, 4-(N,N-dibenzylamino)phenyl, 4-[N,N-bis(2-phenylethyl)amino]phenyl, 4-[N,N-bis(3-phenylpropyl)amino]phenyl, 4-[N,N-bis(4-phenylbutyl)amino]phenyl, 4-[N,N-bis(5-phenylpentyl)amino]phenyl, 4-[N,N-bis(6-phenylhexyl)amino]phenyl, 3-(N,N-dibenzylamino)phenyl, 2-(N,N-dibenzylamino)phenyl, 4-biphenylyl, 3-biphenylyl, 2-biphenylyl, 4-phenoxyphenyl, 3-phenoxyphenyl, 2-phenoxyphenyl, 4-benzyloxyphenyl, 4-(2-phenylethoxy)phenyl, 4-(3-phenylpropoxy)phenyl, 4-(4-phenylbutoxy)phenyl, 4-(5-phenylpentyloxy)phenyl, 4-(6-phenylhexyloxy)phenyl, 3-benzyloxyphenyl, 2-benzyloxyphenyl, 4-trifluoromethylphenyl, 4-pentafluoroethylphenyl, 4-heptafluoropropylphenyl, 4-nonafluorobutylphenyl, 4-undecafluoropentylphenyl, 4-tridecafluorohexylphenyl, 3-trifluoromethylphenyl, 2-trifluoromethylphenyl, 4-trifluoromethoxyphenyl, 4-pentafluoroethoxyphenyl, 4-heptafluoropropoxyphenyl, 4-nonafluorobutoxyphenyl, 4-undecafluoropentyloxyphenyl, 4-tridecafluorohexyloxyphenyl, 3-trifluoromethoxyphenyl, 2-trifluoromethoxyphenyl, 4-dimethoxyphosphorylmethylphenyl, 4-diethoxyphosphorylmethylphenyl, 4-dipropoxyphosphorylmethylphenyl, 4-dibutoxyphosphorylmethylphenyl, 4-dipentyloxyphosphorylmethylphenyl, 4-dihexyloxyphosphorylmethylphenyl, 3-diethoxyphosphorylmethylphenyl, 2-diethoxyphosphorylmethylphenyl, 4-methylthiophenyl, 4-ethylthiophenyl, 4-propylthiophenyl, 4-butylthiophenyl, 4-pentylthiophenyl, 4-hexylthiophenyl, 3-methylthiophenyl, 2-methylthiophenyl, 4-methoxymethylphenyl, 3-methoxymethylphenyl, 2-methoxymethylphenyl, 4-ethoxymethylphenyl, 4-propoxymethylphenyl, 4-butoxymethylphenyl, 4-pentyloxymethylphenyl, 4-hexyloxymethylphenyl, 4-(2-methoxyethyl)phenyl, 4-(3-methoxypropyl)phenyl, 4-(4-methoxybutyl)phenyl, 4-(5-methoxypentyl)phenyl, 4-(6-methoxyhexyl)phenyl, 4-benzyloxymethylphenyl, 3-benzyloxymethylphenyl, 2-benzyloxymethylphenyl, 4-(2-benzyloxyethyl)phenyl, 4-(3-benzyloxypropyl)phenyl, 4-(4-benzyloxybutyl)phenyl, 4-(5-benzyloxypentyl)phenyl, 4-(6-benzyloxyhexyl)phenyl, 4-(2-phenylethoxymethyl)phenyl, 4-(3-phenylpropoxymethyl)phenyl, 4-(4-phenylbutoxymethyl) phenyl, 4-(5-phenylpentyloxymethyl)phenyl, and 4-(6-phenylhexyloxymethyl)phenyl.

The phenyl group which is optionally substituted with a lower alkyl group includes, for example, 2-methylphenyl, 3-methylphenyl, 4-methylphenyl, 2,4-dimethylphenyl, 3,4-dimethylphenyl, 3,5-dimethylphenyl, 3,4,5-trimethylphenyl, 4-ethylphenyl, 4-propylphenyl, 4-butylphenyl, 4-pentylphenyl, and 4-hexylphenyl, in addition to the phenyl group.

The phenyl lower alkyl group includes, for example, benzyl, 2-phenylethyl, 1-phenylethyl, 3-phenylpropyl, 4-phenylbutyl, 5-phenylpentyl, or 6-phenylhexyl.

The phenyl lower alkyl group which optionally has 1 to 3 lower alkoxy groups as a substituent includes, for example, 2-methoxybenzyl, 3-methoxybenzyl, 4-methoxybenzyl, 2,4-dimethoxybenzyl, 3,4-dimethoxybenzyl, 3,5-dimethoxybenzyl, 3,4,5-trimethoxybenzyl, 4-ethoxybenzyl, 4-propoxybenzyl, 4-butoxybenzyl, 4-pentyloxybenzyl, 4-hexyloxybenzyl, 2-(4-methoxyphenyl)ethyl, 3-(4-methoxyphenyl)propyl, 4-(4-methoxyphenyl)butyl, 5-(4-methoxyphenyl)pentyl, 6-(4-methoxyphenyl)hexyl, 2-(3,4,5-trimethoxyphenyl)ethyl, 3-(3,4,5-trimethoxyphenyl)propyl, 4-(3,4,5-trimethoxyphenyl)butyl, 5-(3,4,5-trimethoxyphenyl)pentyl, and 6-(3,4,5-trimethoxyphenyl)hexyl, in addition to the phenyl lower alkyl group described above.

The styryl group which optionally has 1 to 3 lower alkyl groups as a substituent includes, for example, 2-methoxystyryl, 3-methoxystyryl, 4-methoxystyryl, 2,4-dimethoxystyryl, 3,4-dimethoxystyryl, 3,5-dimethoxystyryl, 3,4,5-trimethoxystyryl, 4-ethoxystyryl, 4-propoxystyryl, 4-butoxystyryl, 4-pentyloxystyryl, or 4-hexyloxystyryl, in addition to the styryl group.

Specific examples of the compounds (1) of the present invention are shown in Tables 1 to 8. In the respective tables, Me denotes a methyl group, Et denotes an ethyl group, n-Pr denotes a n-propyl group, n-Bu denotes a n-butyl group, n-Pe denotes a n-pentyl group, n-Hx denotes a n-hexyl group, n-Hp denotes a n-heptyl group, n-Oc denotes a n-octyl group, Ph denotes a phenyl group and Bn denotes a benzyl group, respectively.

TABLE 1

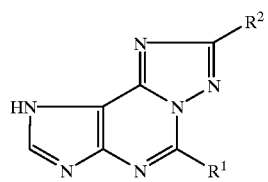

| $R^1$ | $R^2$ | $R^1$ | $R^2$ | $R^1$ | $R^2$ | $R^1$ | $R^2$ |
|---|---|---|---|---|---|---|---|
| Me | 4-Me-C₆H₄ | Me | 2-Cl-C₆H₄ | Me | 2-furyl | Me | 4-pyridyl |

TABLE 1-continued
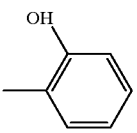
| R¹ | R² | R¹ | R² | R¹ | R² | R¹ | R² |
|---|---|---|---|---|---|---|---|
| Me | 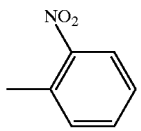 | Me | 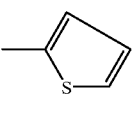 | Me | 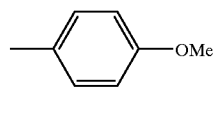 | Me | 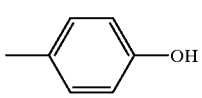 |
| Me | 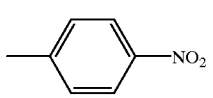 | Me | 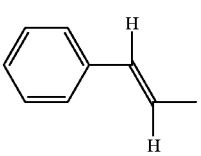 | Me | 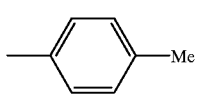 | Et | Ph |
| Et | 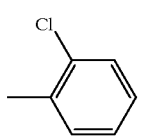 | Et | 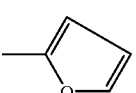 | Et | 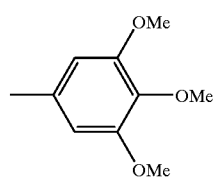 | Et | 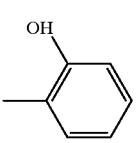 |
| Et | 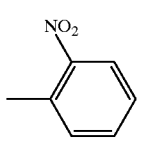 | Et | 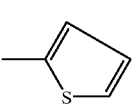 | Et | 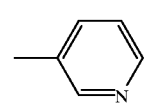 | Et | 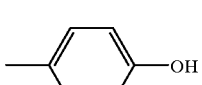 |
| Et | 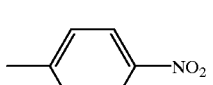 | Et | 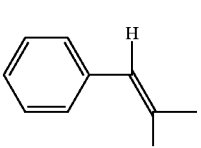 | Et | 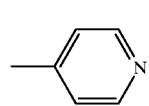 | Et | 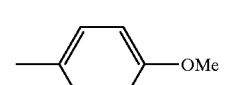 |
| Et | 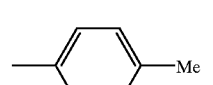 | n-Pr | 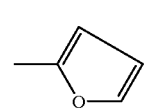 | n-Pr | Ph | n-Pr | 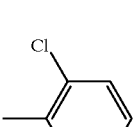 |
| n-Pr | 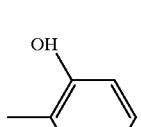 | n-Pr | 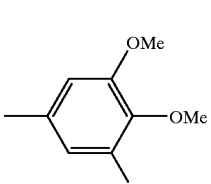 | n-Pr | 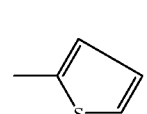 | n-Pr |  |

TABLE 1-continued
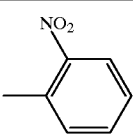
| R¹ | R² | R¹ | R² | R¹ | R² | R¹ | R² |
|---|---|---|---|---|---|---|---|
| n-Pr | 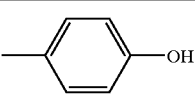 | n-Pr | 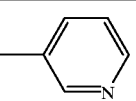 | n-Pr | 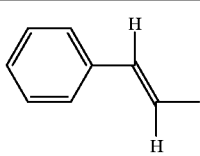 | n-Pr | 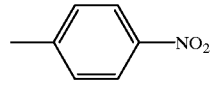 |
| n-Pr | 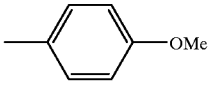 | n-Pr | 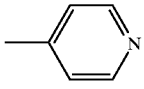 | n-Pr | 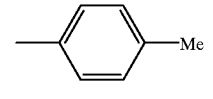 | n-Pe | Ph |
| n-Pe | 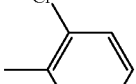 | n-Pe | 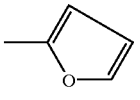 | n-Pe | 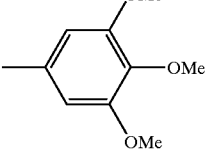 | n-Pe | 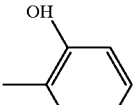 |
(Continued on Table 2)
TABLE 2
| R¹ | R² | R¹ | R² | R¹ | R² | R¹ | R² |
|---|---|---|---|---|---|---|---|
| n-Pe | 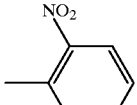 | n-Pe | 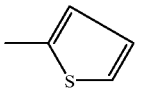 | n-Pe | 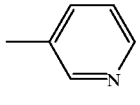 | n-Pe | 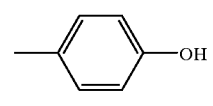 |
| n-Pe | 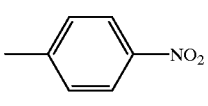 | n-Pe | 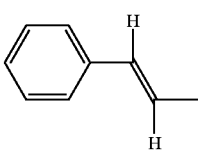 | n-Pe | 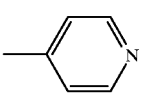 | n-Pe | 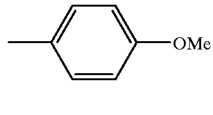 |
| n-Pe | 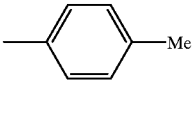 | n-Hx | 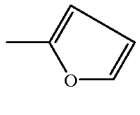 | n-Hx | Ph | n-Hx | 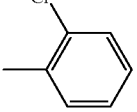 |
| n-Hx | 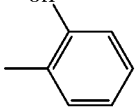 | n-Hx | 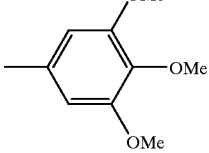 | n-Hx | 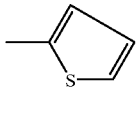 | n-Hx | 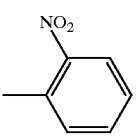 |
| n-Hx | 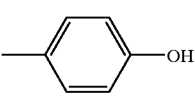 | n-Hx | 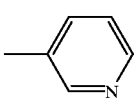 | n-Hx | 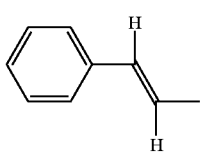 | n-Hx |  |

TABLE 2-continued

| R¹ | R² | R¹ | R² | R¹ | R² | R¹ | R² |
|---|---|---|---|---|---|---|---|
| n-Hx | 4-nitrophenyl | n-Hx | 4-methoxyphenyl | n-Hx | 4-pyridyl | Ph | (E)-styryl (PhCH=CH-) |
| Ph | 4-methylphenyl | Ph | 2-chlorophenyl | Ph | 2-furyl | Ph | 4-pyridyl |
| Ph | 2-hydroxyphenyl | Ph | 2-nitrophenyl | Ph | 2-thienyl | Ph | 4-methoxyphenyl |
| Ph | 4-hydroxyphenyl | Ph | 4-nitrophenyl | Me | 4-chlorophenyl | Et | 4-chlorophenyl |
| n-Pr | 4-chlorophenyl | n-Bu | 4-chlorophenyl | n-Pe | 4-chlorophenyl | n-Hx | 4-chlorophenyl |
| Ph | 4-chlorophenyl | Me | 2,3,4-trimethoxyphenyl | Et | 2,3,4-trimethoxyphenyl | n-Pr | 2,3,4-trimethoxyphenyl |
| n-Bu | 2,3,4-trimethoxyphenyl | n-Pe | 2,3,4-trimethoxyphenyl | n-Hx | 2,3,4-trimethoxyphenyl | Ph | 2,3,4-trimethoxyphenyl |
| Me | 3-methoxyphenyl | Et | 3-methoxyphenyl | n-Pr | 3-methoxyphenyl | n-Bu | 3-methoxyphenyl |

(Continued on Table 3)

TABLE 3

| R¹ | R² | R¹ | R² | R¹ | R² | R¹ | R² |
|---|---|---|---|---|---|---|---|
| n-Pe | 3-methoxyphenyl | n-Hx | 3-methoxyphenyl | Ph | 3-methoxyphenyl | Me | 4-fluorophenyl |
| Et | 4-fluorophenyl | n-Pr | 4-fluorophenyl | n-Bu | 4-fluorophenyl | n-Pe | 4-fluorophenyl |

TABLE 3-continued

| R$^1$ | R$^2$ | R$^1$ | R$^2$ | R$^1$ | R$^2$ | R$^1$ | R$^2$ |
|---|---|---|---|---|---|---|---|
| n-Hx | 4-F-C$_6$H$_4$ | Ph | 4-F-C$_6$H$_4$ | Me | 3-OMe-C$_6$H$_4$ | Et | 3-OMe-C$_6$H$_4$ |
| n-Pr | 3-OMe-C$_6$H$_4$ | n-Bu | 3-OMe-C$_6$H$_4$ | n-Pe | 3-OMe-C$_6$H$_4$ | n-Hx | 3-OMe-C$_6$H$_4$ |
| Ph | 3-OMe-C$_6$H$_4$ | Me | 2-pyridyl | Et | 2-pyridyl | n-Pr | 2-pyridyl |
| n-Bu | 2-pyridyl | n-Pe | 2-pyridyl | n-Hx | 2-pyridyl | Ph | 2-pyridyl |
| Me | Me | Me | Bn | Et | Me | Et | Bn |
| n-Pr | Me | n-Pr | Bn | n-Pe | Me | n-Pe | Bn |
| n-Hx | Me | n-Hx | Bn | n-Hp | Me | n-Hp | Bn |
| n-Oc | Me | n-Oc | Bn | Ph | Me | Ph | Bn |
| n-Hp | 4-NO$_2$-C$_6$H$_4$ | n-Hp | 4-OMe-C$_6$H$_4$ | n-Hp | PhCH=CH- | n-Hp | 4-OH-C$_6$H$_4$ |
| n-Hp | 4-Me-C$_6$H$_4$ | n-Hp | 4-pyridyl | n-Hp | 2-furyl | n-Hp | 3,4,5-(OMe)$_3$-C$_6$H$_2$ |
| n-Hp | 2-thienyl | n-Oc | 4-OH-C$_6$H$_4$ | n-Oc | 4-NO$_2$-C$_6$H$_4$ | n-Oc | 4-OMe-C$_6$H$_4$ |

(Continued on Table 4)

TABLE 4

| R$^1$ | R$^2$ | R$^1$ |
|---|---|---|
| 3-OMe-C$_6$H$_4$ | Me | Me |
| 3-OMe-C$_6$H$_4$ | Bn | Et |

TABLE 4-continued
| | | |
|---|---|---|
| n-Oc | 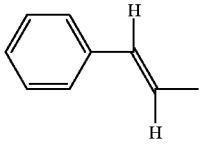 | n-Pr |
| n-Oc | Ph | n-Pe |
| n-Oc | 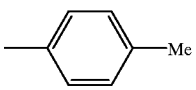 | n-Hx |
| n-Oc | 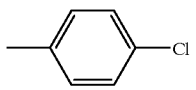 | n-Hp |
| n-Oc | 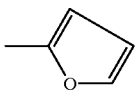 | n-Oc |
| n-Oc | 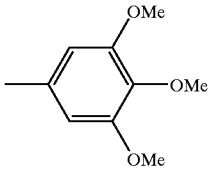 | Ph |
| n-Oc | 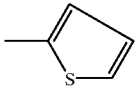 | 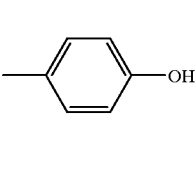 |
| 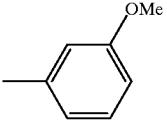 | 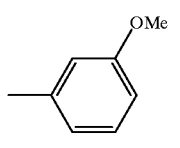 | 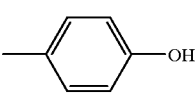 |
| 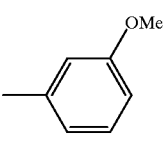 | 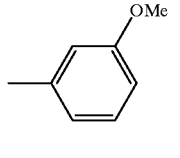 | 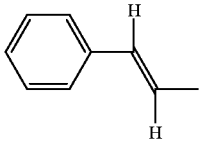 |
| 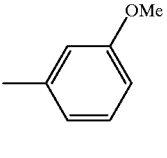 | 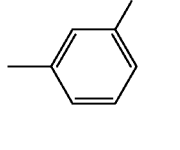 | 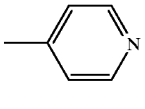 |
| 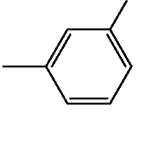 | 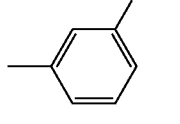 | n-Bu |

TABLE 4-continued
| R² | R¹ | R² |
|---|---|---|
| n-Bu | 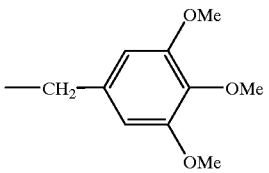 | n-Oc |
| R² | R¹ | R² |
|---|---|---|
| 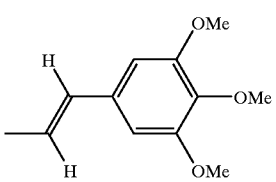 | Me | 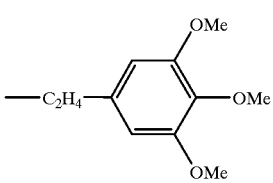 |
| 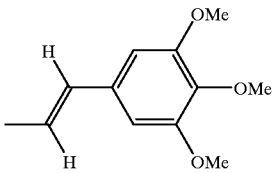 | Et | 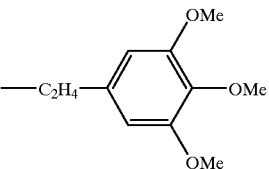 |
| 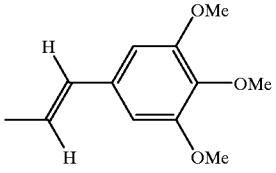 | n-Pr | 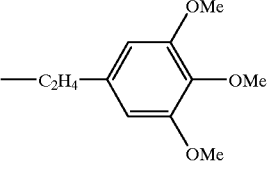 |
| 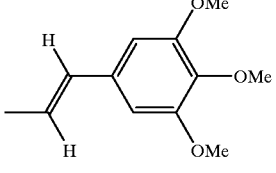 | n-Pe | 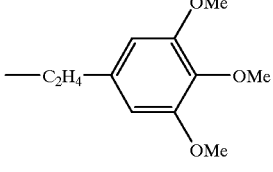 |
| 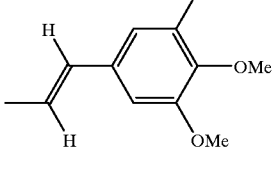 | n-Hx | 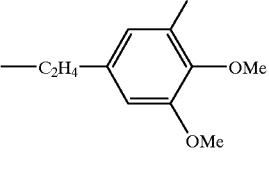 |
| 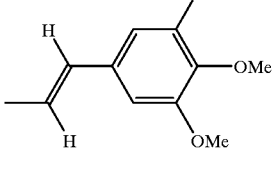 | n-Hp | 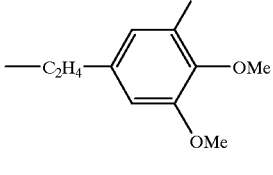 |
| 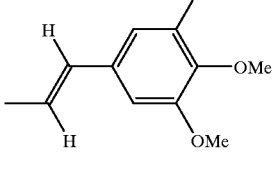 | n-Oc | 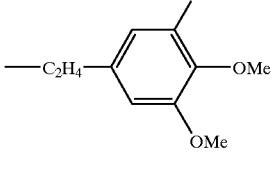 |

TABLE 4-continued
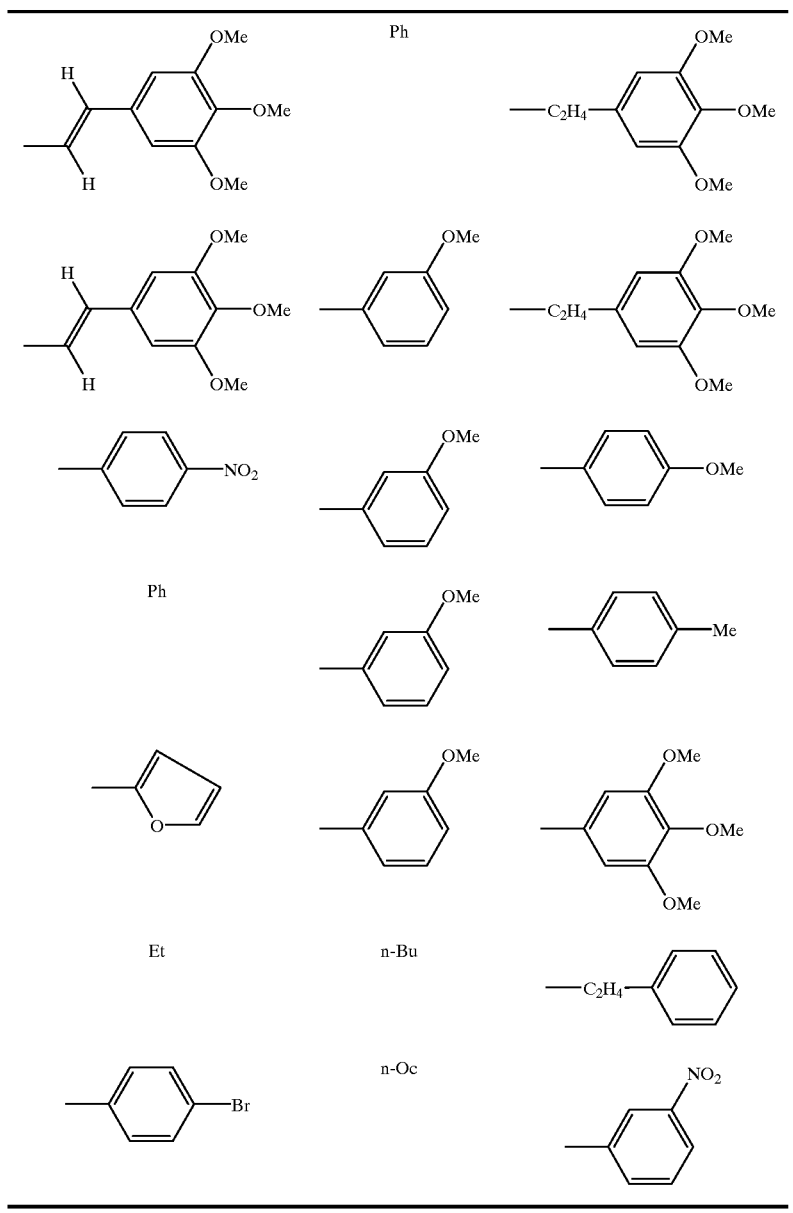
(Continued on Table 5)
TABLE 5
| R¹ | R² | R¹ | R² | R¹ | R² |
|---|---|---|---|---|---|
| Me | -C6H4-Ph | Et | -C6H4-Ph | n-Pr | -C6H4-Ph |
| n-Pe | -C6H4-Ph | n-Hx | -C6H4-Ph | n-Hp | -C6H4-Ph |
| n-Oc | -C6H4-Ph | Me | -C6H4-CF3 | Et | -C6H4-CF3 |

TABLE 5-continued
| R¹ | R² | R¹ | R² | R¹ | R² |
| --- | --- | --- | --- | --- | --- |
| n-Pr | 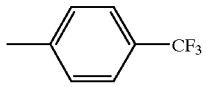 | n-Pe | 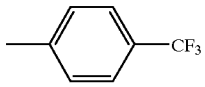 | n-Hx | 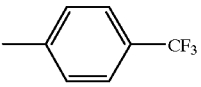 |
| n-Hp | 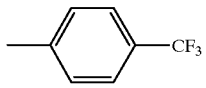 | n-Oc | 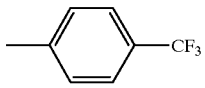 | Me | 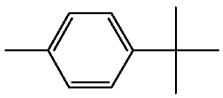 |
| Et | 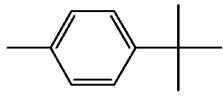 | n-Pr | 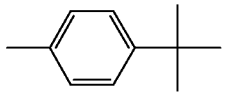 | n-Pe | 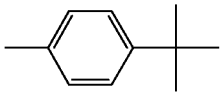 |
| n-Hx | 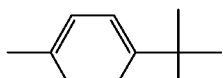 | n-Hp | 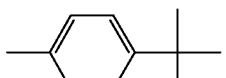 | n-Oc | 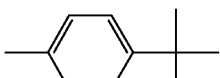 |
| Me |  | Et |  | n-Pr | 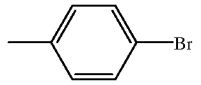 |
| n-Pe | 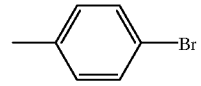 | n-Hx | 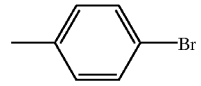 | n-Hp | 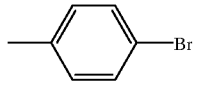 |
| n-Oc | 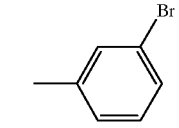 | Me | 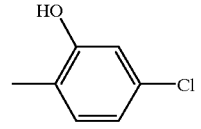 | Et | 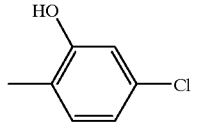 |
| n-Pr | 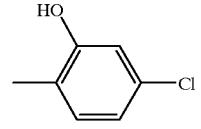 | n-Pe | 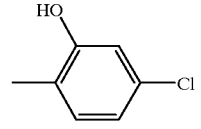 | n-Hx | 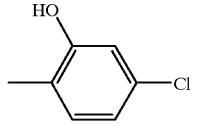 |
| n-Hp | 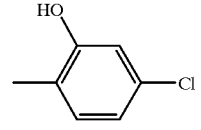 | n-Oc | 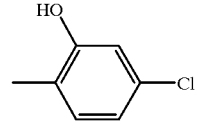 | Me | 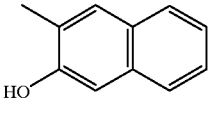 |
| Et | 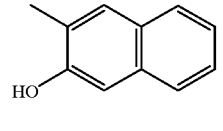 | n-Pr | 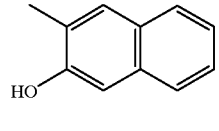 | n-Pe | 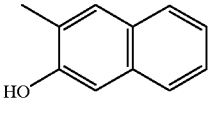 |
| n-Hx | 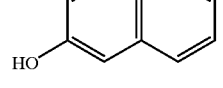 | n-Hp | 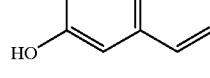 | n-Oc | 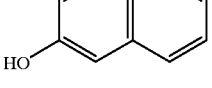 |

TABLE 6
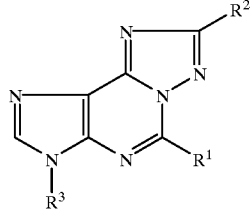
| R¹ | R² | R³ | R¹ | R² | R³ |
|---|---|---|---|---|---|
| Me | Ph | Bn | Me | 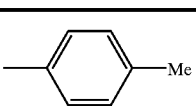 | Bn |
| Me | 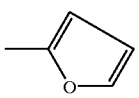 | Bn | Me | 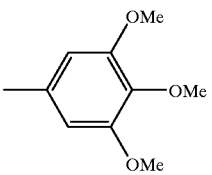 | Bn |
| Me | 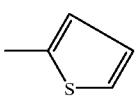 | Bn | Me | 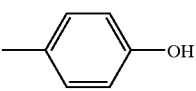 | Bn |
| Me | 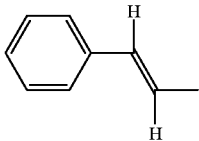 | Bn | Me | 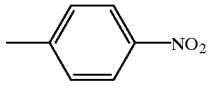 | Bn |
| Me | 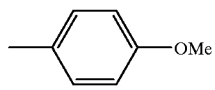 | Bn | Me | 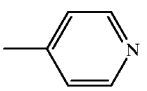 | Bn |
| Me | Me | Bn | Me | Bn | Bn |
| Me | 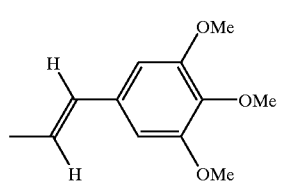 | Bn | Me | —C₂H₄—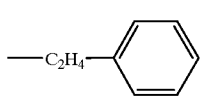 | Bn |
| n-Bu | Ph | —C₂H₄—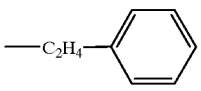 | n-Bu | 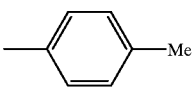 | Bn |
| n-Bu | 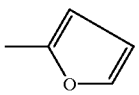 | Bn | n-Bu | 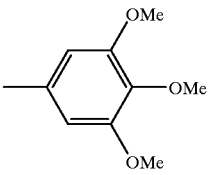 | Bn |
| n-Bu | 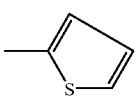 | Bn | n-Bu | 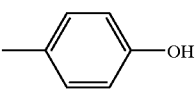 | Bn |

TABLE 6-continued
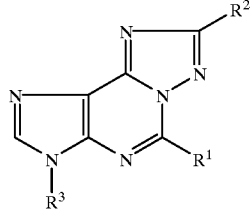
| R¹ | R² | R³ | R¹ | R² | R³ |
|---|---|---|---|---|---|
| n-Bu | 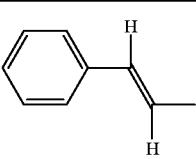 | Bn | n-Bu | 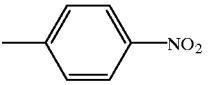 | Bn |
(Continued on Table 7)
TABLE 7
| R¹ | R² | R³ | R¹ | R² | R³ |
|---|---|---|---|---|---|
| n-Bu | 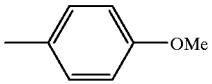 | Bn | n-Bu | 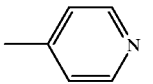 | Bn |
| n-Bu | Me | Bn | n-Bu | Bn | Bn |
| n-Bu | 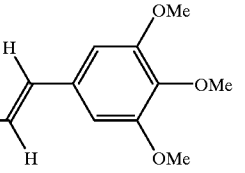 | Bn | n-Bu | 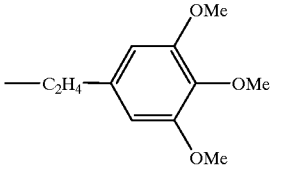 | Bn |
| n-Oc | Ph | Bn | n-Oc | 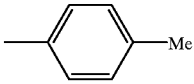 | Bn |
| n-Oc | 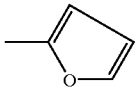 | Bn | n-Oc | 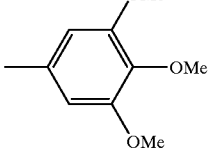 | Bn |
| n-Oc | 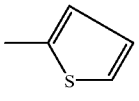 | Bn | n-Oc | 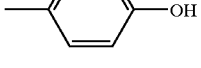 | Bn |
| n-Oc | 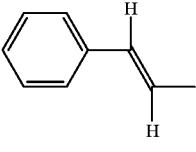 | Bn | n-Oc | 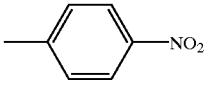 | Bn |
| n-Oc | 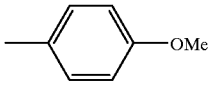 | Bn | n-Oc | 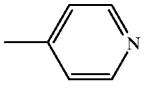 | Bn |

TABLE 7-continued
| R¹ | R² | R³ | R¹ | R² | R³ |
|---|---|---|---|---|---|
| n-Oc | Me | Bn | n-Oc | Bn | Bn |
| n-Oc | 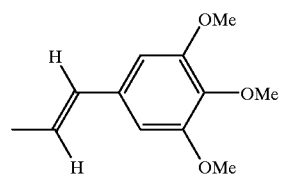 | Bn | n-Oc | 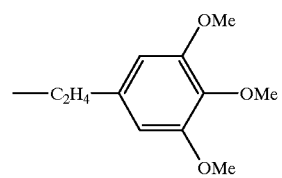 | Bn |
| Ph | Ph | Bn | Ph | 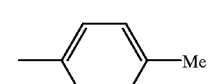 | Bn |
| Ph | 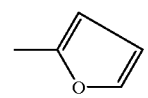 | Bn | Ph | 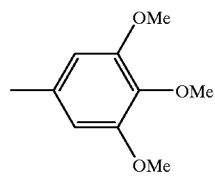 | Bn |
(Continued on Table 8)
TABLE 8
| R¹ | R² | R³ | R¹ | R² | R³ |
|---|---|---|---|---|---|
| Ph | 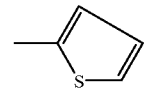 | Bn | Ph | 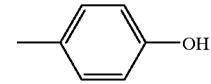 | Bn |
| Ph | 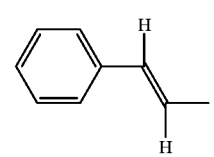 | Bn | Ph |  | Bn |
| Ph |  | Bn | Ph | 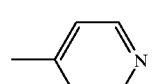 | Bn |
| Ph | Me | Bn | Ph | Bn | Bn |
| Ph | 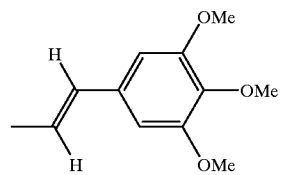 | Bn | Ph | 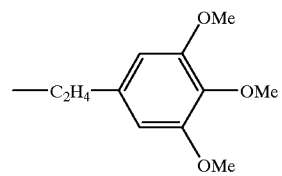 | Bn |
| 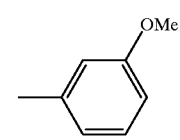 | Ph | Bn | 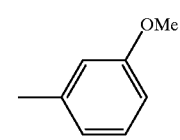 | 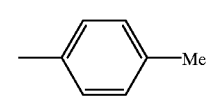 | Bn |

TABLE 8-continued

| R¹ | R² | R³ | R¹ | R² | R³ |
|---|---|---|---|---|---|
| 3-MeO-C₆H₄ | 2-furyl | Bn | 3-MeO-C₆H₄ | 3,4,5-(MeO)₃-C₆H₂ | Bn |
| 3-MeO-C₆H₄ | 2-thienyl | Bn | 3-MeO-C₆H₄ | 4-HO-C₆H₄ | Bn |
| 3-MeO-C₆H₄ | (E)-CH=CH-Ph | Bn | 3-MeO-C₆H₄ | 4-O₂N-C₆H₄ | Bn |
| 3-MeO-C₆H₄ | 4-MeO-C₆H₄ | Bn | 3-MeO-C₆H₄ | 4-pyridyl | Bn |
| 3-MeO-C₆H₄ | Me | Bn | 3-MeO-C₆H₄ | Bn | Bn |
| 3-MeO-C₆H₄ | (E)-C(Me)=CH-3,4,5-(MeO)₃-C₆H₂ | Bn | 3-MeO-C₆H₄ | -C₂H₄-3,4,5-(MeO)₃-C₆H₂ | Bn |

The compound (1) of the present invention can be prepared by the following reaction scheme-1.

Reaction Scheme-1

$$\underset{(2)}{A\begin{pmatrix}CN\\NH_2\end{pmatrix}} \xrightarrow{R^1C(OZ)_3 \atop (3)} \underset{(4)}{A\begin{pmatrix}CN\\N=C(CN)R^1\end{pmatrix}}$$

$$\downarrow R^2-\overset{O}{\underset{\|}{C}}-NH-NH_2 \ (5)$$

-continued $$\underset{(1)}{A\begin{pmatrix}N-N\\ \diagdown\diagup\\N\\ \diagdown\\N\\ \diagdown\\R^1\end{pmatrix}R^2}$$

wherein R¹, R² and A are as defined above, and Z represents a lower alkyl group.

First, a compound represented by the formula (2) is reacted with an orthoester derivative represented by the formula (3) to obtain an imino ester represented by the formula (4).

This reaction is carried out by adding the orthoester derivative (3) in an equimolar amount or more relative to the amount of the compound (2) and heating at a temperature within a range from 50° C. to reflux temperature for about 10 minutes to 5 hours in the absence of a solvent, or in an inert solvent. As the inert solvent, for example, N,N-dimethylformamide (DMF), N,N-dimethylacetamide (DMA), dimethyl sulfoxide (DMSO), methanol, diphenyl ether, xylene, and diethylene glycol dimethyl ether can be used.

The resulting imino ester derivative (4) is reacted with an acyl hydrazine derivative (5), after the ester derivative is purified according to a conventional method or not, to obtain the compounds (1) of the present invention.

This reaction is carried out by adding the acyl hydrazine derivative (5) in an equimolar amount or more relative to the amount of the imino ester derivative (4) in an inert solvent, optionally adding a catalytic amount of 1,8-diazabicyclo[5,4,0]-7-undecene and heating at a temperature within a range from 50° C. to reflux temperature for about 1 to 50 hours. The inert solvent includes the same solvents as those described above. If necessary, the reaction solution may be alkalified by adding an aqueous sodium hydroxide solution and an aqueous potassium hydroxide solution and reacted furthermore at a temperature within a range from 0° C. to room temperature for about 10 minutes to 5 hours after the completion of the heating reaction.

The substituent represented by $R^1$ of the compound (1) of the present invention can be converted into another one by the reaction shown in the following reaction scheme-2.

Reaction Scheme-2

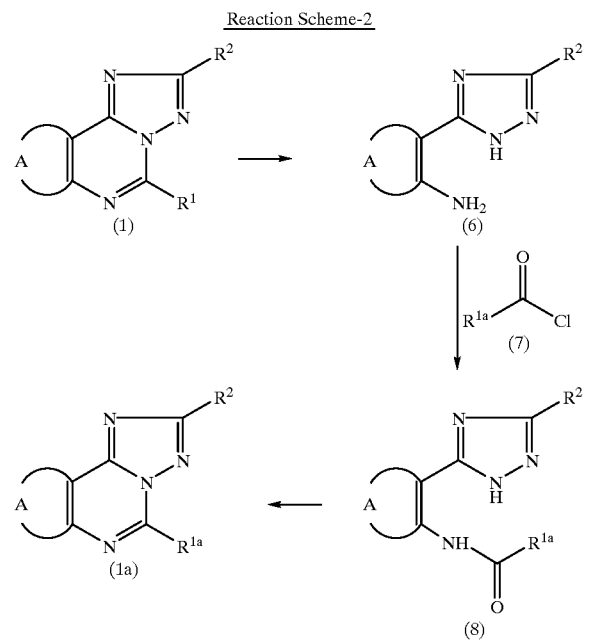

wherein $R^1$, $R^2$ and A are as defined above, and $R^{1a}$ represents a substituent different from $R^1$ within the same definition range as in $R^1$.

First, the compound (1) is converted into an amine compound (6) by refluxing in an aqueous solution of mineral acid such as hydrochloric acid or sulfuric acid for 5 minutes to 1 hour.

Then, the amine compound (6) is acylated. This acylation can be carried out by reacting the amine compound (6) with a carboxylicacid chloride (7) in an amine-based inert solvent such as pyridine, lutidine, triethylamine, or 4-(N,N-dimethylamino)pyridine. In this reaction, the carboxylic acid chloride (7) is used in an equimolar amount or more and the reaction is completed within about 10 minutes to 3 hours at a temperature within a range from 0° C. to room temperature. Since a compound substituted with a plurality of acyl groups may be included sometime in the acylation reaction, the inclusion can optionally be converted into a desired monoacyl compound (8) by refluxing the product, together with a catalytic amount of an alkaline such as anhydrous potassium carbonate or anhydrous sodium carbonate, in an inert solvent such as methanol or ethanol for about 10 minutes to 2 hours.

Subsequently, the monoacyl compound (8) thus obtained is converted into a compound (1a) by the cyclization reaction. The cyclization reaction is carried out by reacting the monoacyl compound (8) with a halogenated trialkylsilane in an inert solvent in the presence of a base.

As the inert solvent, for example, aromatic and aliphatic hydrocarbons such as toluene, xylene, and petroleum ether; ethers such as diethyl ether and tetrahydrofuran; and halogenated hydrocarbons such as dichloromethane, chloroform, carbon tetrachloride, and 1,2-dichloroethane can be used. As the base, for example, tertiary amine such as triethylamine, N,N-diethylaniline, N-methyl morpholine, pyridine, or 4-(N,N-dimethylamino)pyridine can be preferably used. As the halogenated trialkylsilane, for example, chlorotrialkylsilane such as chloromethylsilane, chlorotriethylsilane, chlorotriethyldimethylsilane, chlorodimethylpropylsilane, chlorobutyldimethylsilane, chlorotripropylsilane, tributylchlorosilane, or chloroethylmethylpropylsilane can be preferably used.

The amount of the halogenated trialkylsilane and base to be used is not specifically limited, but is generally controlled to an equal equivalent weight or more, and preferably from 3- to 20-fold equivalent weight relative to the amount of the monoacyl compound (8). The cyclization reaction is usually completed within about 0.5 to 30 hours at a temperature within a range from 0 to 100° C.

The desired object in each process of the reaction scheme can be easily isolated and purified by a conventional separation means. The separation means includes adsorption chromatography, preparative thin-layer chromatography, recrystallization, solvent extraction or the like.

In case of a compound wherein A is a group:

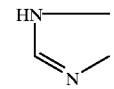

among the compounds (1) of the present invention prepared as described above, it is considered that the compound includes the following four structural formulas as a tautomer and the tautomer can be represented by any of the structural formulas.

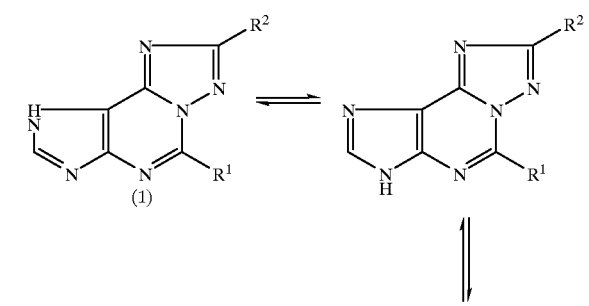

-continued

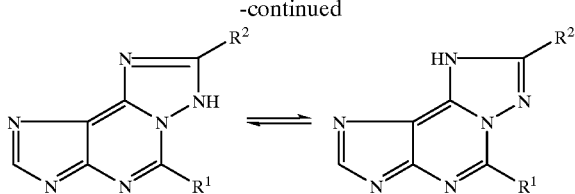

wherein R¹ and R² are as defined above.

A compound wherein R² is a styryl group which optionally has 1 to 3 lower alkoxy groups as a substituent, among the compounds (1) of the present invention, includes geometrical isomers such as E- and Z-isomers. In the present invention, any of both isomers and a mixture thereof may be included. Furthermore, both isomers can be separated by employing the separation means described above.

The compounds (1) of the present invention can be formed into pharmaceutically acceptable acid addition salts, and these salts are also included in the present invention. The acid capable of forming these acid salts includes, for example, inorganic acids such as hydrochloric acid, hydrobromic acid, and sulfuric acid; and organic acids such as oxalic acid, fumaric acid, maleic acid, tartaric acid, citric acid, and p-toluenesulfonic acid. The acid addition salts can be formed by a conventional method.

The compounds of the present invention can be formed into alkaline metal salts such as sodium salt and potassium salt; alkaline earth metal salts such as calcium salt and magnesium salt; and copper salts, and these salts can also be included in the present invention.

The compounds (1) of the present invention are used in the form of a general pharmaceutical preparation by using, together with a suitable non-toxic preparation carrier. The preparation carrier include diluents and excipients, such as fillers, extenders, binders, humectants, disintegrators, surfactants, and lubricants, which are usually used according to the service form of the preparation, and these are appropriately selected and used according to the unit dosage form of the resulting preparation.

As the unit dosage form of the pharmaceutical preparation using the compound (1), various forms can be selected according to the therapeutic purposes and typical examples thereof include tablets, pills, powders, liquid preparations, suspensions, emulsions, granules, capsules, suppositories, injections (e.g. liquid preparations, suspensions, etc.), and ointments.

In case of forming into the form of tablets, there can be used, as the preparation carrier, excipients such as lactose, sucrose, sodium chloride, glucose, urea, starch, calcium carbonate, kaolin, crystalline cellulose, silicic acid, and potassium phosphate; binders such as water, ethanol, propanol, simple syrup, glucose solution, starch solution, gelatin solution, carboxymethylcellulose, hydroxypropylcellulose, methylcellulose, and polyvinyl pyrrolidone; disintegrators such as sodium carboxymethylcellulose, calcium carboxymethylcellulose, low substituted hydroxypropylcellulose, dried starch, sodium alginate, agar powder, laminaran powder, sodium hydrogencarbonate, and calcium carbonate; surfactants such as polyoxyethylene sorbitan fatty acid esters, sodium lauryl sulfate, and monoglyceride stearate; disintegration inhibitors such as sucrose, stearin, cacao butter, and hydrogenated oil; absorption accelerators such as quaternary ammonium base and sodium lauryl sulfate; humectants such as glycerin and starch; adsorbents such as starch, lactose, kaolin, bentonite, and colloidal silicic acid; and lubricants such as purified talc, stearate, powdered boric acid, and polyethylene glycol.

If necessary, tablets can be formed into tablets coated with a common coating, for example, sugar-coated tablets, gelatin-coated tablets, enteric coated tablets, film coating tablets, double layered tablets, or mutilayer tablets.

In case of forming into the form of pills, there can be used, as the preparation carrier, excipients such as glucose, lactose, starch, cacao butter, hardened vegetable oil, kaolin, and talc; binders such as gum arabic, powdered tragacanth, gelatin, and ethanol; and disintegrators such as laminaran and agar.

In case of forming into the form of suppositories, there can be used, as the preparation carrier, polyethylene glycol, cacao butter, higher alcohol, esters of higher alcohol, gelatin, and semi-synthesized glyceride.

Capsules are usually prepared by mixing the compound (1) of the present invention with various pharmaceutical preparations and filling a hard gelatin capsule or a soft gelatin capsule with the mixture.

In case of preparing as injections such as liquid preparations, emulsions or suspension, these are preferably sterilized and are isotonic with blood. In case of forming into the form of injections, there can be used, as the diluent, water, ethyl alcohol, propylene glycol, ethoxylated isostearyl alcohol, polyoxylated isostearyl alcohol, or polyoxyethylene sorbitan fatty acid esters. In this case, salt, glucose or glycerin may be contained in an enough amount to prepare an isotonic solution and common solubilizers, buffer agents or soothing agents may also be added.

If necessary, the pharmaceutical preparation further contains colorants, preservatives, perfumes, flavors, sweeteners, or other drugs.

In case of forming into the form such as paste, cream, or gel, there can be used, as the diluent, white soft paraffin, paraffin, glycerin, cellulose derivative, polyethylene glycol, silicon, and bentonite.

The amount of the compound (1) of the present invention to be incorporated in the pharmaceutical preparation is not specifically limited and appropriately selected from a wide range, but is preferably within a range from about 1 to 85% by weight based on the pharmaceutical preparation.

The administration method of the pharmaceutical preparation is not specifically limited, but is appropriately decided according to the form of preparations, age of patients, sex and other conditions, or conditions of diseases. For example, tablets, pills, liquid preparations, suspensions, granules and capsules are orally administered, while injections are intravenously administered alone or in comnination with a conventional replenisher such as glucose or amino acid, or intramascularly, intracutaneously, subctaneously or intraperitoneally administered alone, if necessary. Furthermore, suppositories are intrarectally administered.

The dose of the pharmaceutical preparation varies depending on the administration method, age of patients, sex and other conditions, or conditions of diseases, but a dairy dose of the compound (1) of the present invention is usually within a range from about 0.5 to 20 mg/kg, and preferably from about 1 to 10 mg/kg. The pharmaceutical preparation can be administered 1 to 4 times per day.

Industrial Applicability

It is expected that the triazolopurine derivative of the present invention is applied to antihypertensive, antiallergic agent, anti-inflammatory agent, remedy for ischemic heart disease, remedy for leukemia, antipruritic, expectorant, cough medicine, remedy for asthma, and analgesic because of its affinity to an adenosine A3 receptor.

EXAMPLES

The following Reference Examples, Examples, Experiment and Preparation Examples further illustrate the compounds of the present invention in detail.

Reference Example 1

Preparation of Methyl N-(5-cyanoimidazol-4-yl)acetimidate 5 g of 4-amino-5-cyanoimidazole was suspended in 10 mL of DMF and 10 mL of trimethyl orthoacetate was added, followed by stirring at 90° C. for 30 minutes. The reaction solution was concentrated under reduced pressure and the residue was dilute with ethyl acetate, and then 4.2 g of desired compound deposited as a crystal was collected by filtration. The solution was concentrated and the residue was purified by silica gel column chromatograpy (eluent: ethyl acetate) and then recrystallized from ethyl acetate-n-hexane to obtain 2.9 g of a desired compound as a crystal.

Melting point: 147–149° C.

Reference Example 2

In the same manner as in Reference Example 1, methyl N-(5-cyanoimidazol-4-yl)pentanimidate was prepared.

Melting point: 114–116° C.

Reference Example 3

In the same manner as in Reference Example 1, methyl N-(5-cyanoimidazol-4-yl)benzimidate was prepared.

Melting point: 157–159° C.

In the same manner as in Reference Example 1, the following compounds could be prepared.
— Methyl N-(5-cyanoimidazol-4-yl)propionimidate
— Methyl N-(5-cyanoimidazol-4-yl)butyrimidate
— Methyl N-(5-cyanoimidazol-4-yl)hexanimidate
— Methyl N-(5-cyanoimidazol-4-yl)heptanimidate
— Methyl N-(5-cyanoimidazol-4-yl)octanimidate
— Methyl N-(5-cyanoimidazol-4-yl)nonanimidate
— Methyl N-(5-cyanoimidazol-4-yl)-3-methylbenzimidate

Reference Example 4

In the same manner as in Reference Example 1, except for using 5-amino-1-benzyl-4-cyanoimidazole as a starting material, the following respective compounds were prepared.
— Methyl N-(1-benzyl-4-cyanoimidazol-5-yl)acetimidate
— Methyl N-(1-benzyl-4-cyanoimidazol-5-yl)propionimidate
— Methyl N-(1-benzyl-4-cyanoimidazol-5-yl)butyrimidate
— Methyl N-(1-benzyl-4-cyanoimidazol-5-yl)pentanimidate
— Methyl N-(1-benzyl-4-cyanoimidazol-5-yl)hexanimidate
— Methyl N-(1-benzyl-4-cyanoimidazol-5-yl)heptanimidate
— Methyl N-(1-benzyl-4-cyanoimidazol-5-yl)octanimidate
— Methyl N-(1-benzyl-4-cyanoimidazol-5-yl)nonanimidate
— Methyl N-(1-benzyl-4-cyanoimidazol-5-yl)benzimidate
— Methyl N-(1-benzyl-4-cyanoimidazol-5-yl)-3-methylbenzimidate

Reference Example 5

In the same manner as in Reference Example 1, except for using 4-amino-1-benzyl-5-cyanoimidazole, 5-amino-4-cyano-1-methylimidazole, 4-amino-5-cyano-1-methylimidazole, 5-amino-4-cyano-1-ethylimidazole and 4-amino-5-cyano-1-ethylimidazole as a starting material, the following respective compounds were prepared.
— Methyl N-(1-benzyl-5-cyanoimidazol-4-yl)heptanimidate
— Methyl N-(5-cyano-1-methylimidazol-4-yl)heptanimidate
— Methyl N-(4-cyano-1-methylimidazol-5-yl)heptanimidate
— Methyl N-(5-cyano-1-ethylimidazol-4-yl)heptanimidate
— Methyl N-(4-cyano-1-ethylimidazol-5-yl)heptanimidate

Example 1

Preparation of 5-methyl-8-phenyl-1H-1,2,4-triazolo[5,1-i]purine 4.0 g of methyl N-(5-cyanoimidazol-4-yl)acetimidate obtained in Reference Example 1 and 3.65 g of N-benzoylhydrazine were dissolved in 40 mL of DMF, followed by stirring at 80° C. for one hour and further stirring at 150° C. for 15 hours. The reaction solution was air-cooled to room temperature and the pH of the solution was adjusted within a range from 9 to 10 by adding dropwise 13 mL of an aqueous 10% sodium hydroxide solution, followed by stirring at room temperature for one hour. After the completion of the reaction, 10% hydrochloric acid and water were added in turn thereby to adjust the pH to 3. The deposited crystal was collected by filtration and washed with hot ethanol to obtain 5.5 g of a desired compound as a crystal. The structure and melting point of the resulting desired compound are shown in Table 9.

Examples 2 to 20

In the same manner as in Example 1, except for using any one of the respective compounds obtained in Reference Examples 1 to 3 described above and a predetermined acyl hydrazine derivative, the respective compounds having the structures and melting points shown in Tables 9 and 10 were prepared. In Tables 9 and 10, Me denotes a methyl group, n-Bu denotes a n-butyl group and Ph denotes a phenyl group, respectively.

TABLE 9

| Example No. | $R^1$ | $R^2$ | Melting point (° C.) |
|---|---|---|---|
| 1 | Me | Ph | >285 |
| 2 | Me | 2,4,5-tri(OMe)phenyl | 248–251 |

TABLE 9-continued

[Structure: fused bicyclic heterocycle with R¹ and R² substituents, 1H-imidazo-triazolo-pyrimidine type]

| Example No. | R¹ | R² | Melting point (°C) |
|---|---|---|---|
| 3 | Me | 3-pyridyl | >285 |
| 4 | n-Bu | Ph | 238~240 |
| 5 | n-Bu | 4-Me-C₆H₄ | 254~255 |
| 6 | n-Bu | 2-OH-C₆H₄ | 217~219 |
| 7 | n-Bu | 4-OH-C₆H₄ | >285 |
| 8 | n-Bu | 4-OMe-C₆H₄ | 195~200 (Na salt) |
| 9 | n-Bu | 2-Cl-C₆H₄ | 177~179 |
| 10 | n-Bu | 2-NO₂-C₆H₄ | 155~157 |

(Continued on Table 10)

TABLE 10

| Example No. | R¹ | R² | Melting Point (°C) |
|---|---|---|---|
| 11 | n-Bu | 4-NO₂-C₆H₄ | 269~270 |
| 12 | n-Bu | 3,4,5-tri-OMe-C₆H₂ | 191~193 |
| 13 | n-Bu | 3-pyridyl | >220 (decomposed) |
| 14 | n-Bu | 4-pyridyl | 287~288 |
| 15 | n-Bu | 2-furyl | 255~256 |
| 16 | n-Bu | 2-thienyl | 243~244 |
| 17 | n-Bu | (E)-CH=CH-Ph (styryl) | 209~211 |
| 18 | Ph | Ph | 268~269 |
| 19 | Ph | 3,4,5-tri-OMe-C₆H₂ | 251~252 |
| 20 | Ph | 3-pyridyl | 279~281 |

The measurement results of NMR of the resulting respective compounds are shown below.

Compound of Example 1

$^1$H-NMR(DMSO-$d_6$) δ: 3.03 (3H, s), 7.5–7.7 (3H, m), 8.3–8.4 (2H, m), 8.48 (1H, s), 13.6–14.1 (1H, brs).

Compound of Example 2

$^1$H-NMR(DMSO-d$_6$) δ: 2.98 (3H, s), 3.76 (3H, s), 3.92 (6H, s), 7.56 (2H, s), 8.42 (1H, s), 13.6–14.1 (1H, brs).

Compound of Example 3

$^1$H-NMR(DMSO-d$_6$) δ: 3.05 (3H, s), 7.69 (1H, dd, J=4.9, 7.9), 8.50 (1H, s), 8.65 (1H, d, J=7.9), 8.81 (1H, d, J=4.9), 9.49(1H, s), 13.5–14.1 (1H, brs).

Compound of Example 4

$^1$H-NMR(DMSO-d$_6$) δ: 1.05 (3H, t, J=7.4), 1.5–1.6 (2H, m), 1.9–2.1 (2H, m), 3.43 (2H, t, J=7.4), 7.6–7.7 (3H, m), 8.3–8.4 (2H, m), 8.50 (1H, s), 13.6–14.2 (1H, brs).

Compound of Example 5

$^1$H-NMR(DMSO-d$_6$) δ: 0.98 (3H, t, J=7.4), 1.4–1.6 (2H, m), 1.8–2.0 (2H, m), 2.40 (3H, s), 3.35 (2H, t, J=7.4), 7.38 (2H, d, J=7.9), 8.16 (2H, d, J=7.9), 8.42 (1H, s), 13.5–14.0 (1H, brs).

Compound of Example 6

$^1$H-NMR(DMSO-d$_6$) δ: 0.98 (3H, t, J=7.2), 1.4–1.6 (2H, m), 1.8–2.0 (2H, m), 3.36 (2H, t, J=7.7), 7.0–7.1 (2H, m), 7.42 (1H, t, J=8.2), 8.17 (1H, d, J=7.9), 8.48 (1H, s), 11.21 1H, s), 13.7–14.1 (1H, brs).

Compound of Example 7

$^1$H-NMR(DMSO-d$_6$) δ: 0.98 (3H, t, J=7.4),1.4–1.6 (2H, m), 1.9–2.0 (2H, m), 3.34 (2H, t, J=6.9), 6.94 (2H, d, J=8.9), 8.11 (2H, d, J=8.9), 8.40 (1H, s), 9.7–10.2 (1H, brs) 13.3–14.2 (1H, brs).

Compound of Example 8

$^1$H-NMR(DMSO-d$_6$) δ: 1.04 (3H, t, J=7.4), 1.4–1.6 (2H, m), 1.9–2.1 (2H, m), 3.37 (2H, t, J=7.4), 3.92 (3H, s), 7.17 (2H, d, J=7.9), 8.17 (1H, s), 8.27 (2H, d, J=7.9).

Compound of Example 9

$^1$H-NMR(DMSO-d$_6$) δ: 0.96 (3H, t, J=7.4), 1.4–1.5 (2H, m), 1.9–2.0 (2H, m), 3.36 (2H, t, J=7.5), 7.5–7.7 (3H, m) 8.0–8.2 (1H, m), 8.47 (1H, s).

Compound of Example 10

$^1$H-NMR(DMSO-d$_6$) δ: 0.96 (3H, t, J=6.9), 1.4–1.5 (2H, m), 1.8–2.0 (2H, m), 3.30 (2H, t, J=7.4), 7.81 (1H, t, J=7.9), 7.89 (1H, t, J=7.9 ), 8.03 (1H, d, J=7.9), 8.21 (1H, d, J=7.9), 8.46 (1H, s), 13.7–14.1 (1H, brs).

Compound of Example 11

$^1$H-NMR(DMSO-d$_6$) δ: 0.99 (3H, t, J=6.9), 1.4–1.6 (2H, m), 1.8–2.0 (2H, m), 3.33 (2H, t, J=7.9), 8.37 (2H, d, J=8.9), 8.43 (1H, s), 8.45 (2H, d, J=8.9).

Compound of Example 12

$^1$H-NMR(DMSO-d$_6$) δ: 1.04 (3H, t, J=7.4), 1.5–1.6 (2H, m), 2.0–2.1 (2H, m), 3.48 (2H, t, J=7.4), 3.95 (3H, s), 4.00 (6H, s), 7.65 (2H, s), 8.19 (1H, s).

Compound of Example 13

$^1$H-NMR(DMSO-d$_6$) δ: 0.98 (3H, t, J=7.4), 1.4–1.6 (2H, m), 1.8–2.0 (2H, m), 3.38 (2H, t, J=7.4), 7.62 (1H, dd, J=5.0, 7.9), 8.44 (1H, s), 8.59 (1H, d, J=7.9), 8.75 (1H, d, J=5.0), 9.42 (1H, s).

Compound of Example 14

$^1$H-NMR(DMSO-d$_6$) δ: 0.99 (3H, t, J=6.9), 1.4–1.6 (2H, m), 1.9–2.0 (2H, m), 3.38 (2H, t, J=7.4), 8.18 (2H, d, J=5.9), 8.46 (1H, s), 8.81 (2H, d, J=5.9).

Compound of Example 15

$^1$H-NMR(DMSO-d$_6$) δ: 0.97 (3H, t, J=7.4), 1.4–1.5 (2H, m), 1.8–2.0 (2H, m), 3.33 (2H, t, J=7.4), 6.75 (1H, dd, J=2.0, 3.5), 7.29 (1H, brd, J=3.5), 7.97 (1H, brs), 8.43 (1H, s), 13.6–14.0 (1H, brs).

Compound of Example 16

$^1$H-NMR(DMSO-d$_6$) δ: 0.98 (3H, t, J=6.9), 1.4–1.6 (2H, m), 1.8–2.0 (2H, m), 3.32 (2H, t, J=7.4), 7.27 (1H, dd, J=3.5, 4.9), 7.80 (1H, dd, J=1.0, 4.9), 7.92 (1H, dd, J=1.0, 3.5), 8.43 (1H, s), 13.5–14.1 (1H, brs).

Compound of Example 17

$^1$H-NMR(DMSO-d$_6$) δ: 0.96 (3H, t, J=7.4), 1.4–1.5 (2H, m), 1.8–2.0 (2H, m), 3.30 (2H, t, J=7.8), 7.3–7.5 (4H, m), 7.7–7.8 (2H, m), 7.87 (1H, d, J=16.3), 8.41 (1H, s), 13.5–14.0 (1H, brs).

Compound of Example 18

$^1$H-NMR(DMSO-d$_6$) δ: 7.5–7.6 (3H, m), 7.6–7.7 (3H, m), 8.2–8.3 (2H, m), 8.4–8.5 (2H, m), 8.54 (1H, s), 13.7–14.2 (1H, brs).

Compound of Example 19

$^1$H-NMR(DMSO-d$_6$) δ: 3.84 (3H, s), 3.97 (6H, s), 7.59 (2H, s), 7.7–7.8 (3H, m), 8.5–8.6 (2H, m), 8.58 (1H, s).

Compound of Example 20

$^1$H-NMR(DMSO-d$_6$) δ: 7.6–7.7 (4H, m), 8.5–8.6 (4H, m), 8.7–8.8 (1H, m), 9.43 (1H, s).

Examples 21 to 33 and 38 to 40

In the same manner as in Example 1, except for using any one of the respective compounds obtained in Reference Examples 1 to 4 described above and a predetermined acyl hydrazine derivative, the respective compounds having the structures and melting points shown in Tables 11 and 12 were prepared.

Example 34

Preparation of 5-pentyl-8-phenyl-1H-1,2,4-triazolo [5,1-i]purine 4.4 g of the compound obtained in Example 1 was added to a solution of 20 mL of concentrated hydrochloric acid in 50 mL of water, and then the solution was heated at reflux for 30 minutes. The reaction solution was cooled to room temperature and aqueous 25% ammonia was added thereby to adjust the pH to 8. The deposited crystal was collected by filtration and recrystallized from 75% ethanol to obtain 2.58 g of 3-(4-aminopyrazol-5-yl)-5-phenyl-1,2,4-triazole as a crystal.

2 g of the crystal thus obtained was dissolved in 20 mL of pyridine and 4.16 g of hexanoyl chloride was added dropwise at 0° C., followed by stirring at 0° C. for 30 minutes and further stirring at room temperature for 30 minutes. The reaction solution was diluted with ethyl acetate, washed in turn with aqueous citric acid, aqueous sodium hydrogencarbonate and saturated saline, dried over anhydrous magnesium sulfate, and then dried under reduced pressure. The residue was purified by silica gel column chromatography (as an eluent, chloroform was used and then a mixture of chloroform and methanol (30:1) was used) to obtain 5 g of an oily substance. This oily substance was dissolved in 40 mL of ethanol and 10 mg of anhydrous potassium carbonate was added, followed by heating at reflux for 30 minutes. After cooling the reaction solution to room temperature, the deposited crystal was collected by filtration, washed with ethanol and dried to obtain 1.9 g of 3-[4-(N-hexanoylamino)pyrazol-5-yl]-5-phenyl-1,2,4-triazole as a crystal.

Subsequently, 0.4 g of the crystal thus obtained was suspended in 8 mL of tetrahydrofuran and 1.77 mL of triethylamine and 0.63 mL of chlorotrimethylsilane were added, followed by heating at reflux for 20 hours. After the completion of the reaction, iced water and 2 g of citric acid were added in turn and the reaction solution was extracted with ethyl acetate. The organic layer was collected, washed in turn with water and saturate saline, dried over anhydrous magnesium sulfate, and then concentrated under reduced pressure. The residue was purified by silica gel column chromatography (as an eluent, chloroform was used and then a mixture of chloroform and methanol (25:1) was used) and recrystallized from methanol-water to obtain 0.15 g of a desired compound as a crystal. The structure and melting point of the resulting desired compound are shown in Table 12.

Examples 35 to 37

In the same manner as in Example 34, the respective compounds having the structures and melting points shown in Table 12 were prepared.

In Tables 11 and 12, Me denotes a methyl group, Et denotes an ethyl group, n-Pr denotes a n-propyl group, n-Bu denotes a n-butyl group, n-Pe denotes a n-pentyl group, n-Hx denotes a n-hexyl group, n-Hp denotes a n-heptyl group, Ph denotes a phenyl group and Bn denotes a benzyl group, respectively.

TABLE 11

| Example No. | A | $R^1$ | $R^2$ | Melting point (° C.) |
|---|---|---|---|---|
| 21 | HN–CH=N (imidazoline) | n-Bu | 4-Cl-phenyl | 273–275 |
| 22 | " | Et | Ph | 253–255 |
| 23 | " | n-Pr | Ph | 230–233 |

TABLE 11-continued

| Example No. | A | $R^1$ | $R^2$ | Melting point (° C.) |
|---|---|---|---|---|
| 24 | " | Et | 3,4,5-tri-OMe-phenyl | 258–260 |
| 25 | " | n-Bu | 3-Cl-phenyl | 218–221 |
| 26 | " | n-Bu | 3-OMe-phenyl | 183–185 |
| 27 | " | n-Bu | 4-OMe-phenyl | 237–240 |
| 28 | " | n-Bu | 3-Me-phenyl | 201–204 |
| 29 | " | n-Bu | Me | 252–254 |
| 30 | " | n-Bu | Bn | 197–200 |

(Continued on Table 12)

TABLE 12

| Example No. | A | R¹ | R² | Melting point (° C.) |
|---|---|---|---|---|
| 31 |  | n-Bu | 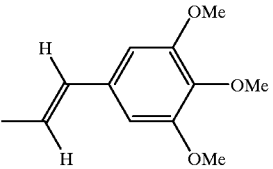 | 238–240 |
| 32 | " | n-Bu | 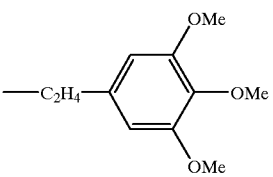 | 179–180 |
| 33 | 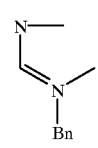 | n-Bu | Ph | 197–199 |
| 34 |  | n-Pe | Ph | 219–220 |
| 35 | " | 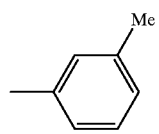 | Ph | 239–241 |
| 36 | " | n-Hx | Ph | 205–209 |
| 37 | " | n-Hp | Ph | 200–203 |
| 38 | " | n-Bu | 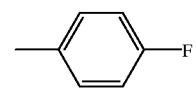 | 259–260 |
| 39 | " | n-Bu | 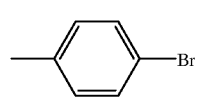 | 280–282 |
| 40 | " | n-Bu | 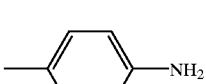 | 245–248 |

The measurement results of NMR of the resulting respective compounds are shown below.

Compound of Example 21

$^1$H-NMR(DMSO-d$_6$) δ: 0.98 (3H, t, J=76.9), 1.4–1.6 (2H, m), 1.8–2.0 (2H, m), 3.35 (2H, t, J=7.4), 7.64 (2H, d, J=8.4), 8.27 (2H, d, J=8.4)s, 8.43 (1H, s), 13.6–14.0 (1H, s, brs).

Compound of Example 22

$^1$H-NMR(DMSO-d$_6$) δ: 1.46 (3H, t, J=7.4), 3.39 (2H, q, J=7.4), 7.5–7.7 (3H, m), 8.2–8.3 (2H, m), 8.43 (1H, s), 13.6–14.0 (1H, brs).

Compound of Example 23

$^1$H-NMR(DMSO-d$_6$) δ: 1.07 (3H, t, J=7.4), 1.9–2.1 (2H, m), 3.33(2H, t, J=7.7), 7.5–7.7 (3H, m), 8.2–8.3 (2H, m), 8.43(1H, s).

Compound of Example 24

$^1$H-NMR(DMSO-d$_6$) δ: 1.46 (3H, t, J=7.4), 3.40 (2H, q, J=7.4), 3.76 (3H, s), 3.92 (6H, s), 7.56 (2H, s), 8.43 (1H, s), 13.6–14.0 (1H, brs).

Compound of Example 25

$^1$H-NMR(DMSO-d$_6$) δ: 0.98 (3H, t, J=7.2), 1.4–1.6 (2H, m), 1.8–2.0 (2H, m), 3.34 (2H, t, J=7.7), 7.6–7.7 (2H, m), 8.2–8.3 (2H, m), 8.43 (1H, s).

Compound of Example 26

¹H-NMR(DMSO-d₆) δ: 0.98 (3H, t, J=7.2), 1.4–1.6 (2H, m), 1.9–2.0 (2H, m), 3.36 (2H, t, J=7.9), 3.88 (3H, s), 7.12 (1H, d, J=8.4), 7.49 (1H, dd, J=7.7, 8.4), 7.79 (1H, s), 7.86 (1H, d, J=7.7), 8.43 (1H, s), 13.6–14.0 (1H, brs).

Compound of Example 27

¹H-NMR(DMSO-d₆) δ: 0.98 (3H, t, J=7.4), 1.4–1.6 (2H, m), 1.8–2.0 (2H, m), 3.34 (2H, t, J=7.4), 3.86 (3H, s), 7.11 (2H, d, J=8.9), 8.20 (2H, d, J=8.9), 8.41 (1H, s).

Compound of Example 28

¹H-NMR(DMSO-d₆) δ: 0.98 (3H, t, J=7.2), 1.4–1.6 (2H, m), 1.8–2.0 (2H, m), 2.43 (3H, s), 3.34 (2H, t, J=7.7), 7.35 (1H, d, J=7.7), 7.45 (1H, t, J=7.7), 8.07 (1H, d, J=7.7), 8.08 (1H, s), 8.42 (1H, s), 13.5–14.0 (1H, brs).

Compound of Example 29

¹H-NMR(DMSO-d₆) δ: 0.95 (3H, t, J=7.2), 1.3–1.5 (2H, m), 1.8–2.0 (2H, m), 2.54 (3H, s), 3.25 (2H, t, J=7.9), 8.38 (1H, s).

Compound of Example 30

¹H-NMR(DMSO-d₆) δ: 0.95 (3H, t, J=7.2), 1.3–1.5 (2H, m), 1.8–2.0 (2H, m), 3.28 (2H, t, J=7.9), 4.25 (2H, s), 7.2–7.5 (5H, m), 8.38 (1H, s).

Compound of Example 31

¹H-NMR(DMSO-d₆) δ: 0.96 (3H, t, J=7.4), 1.3–1.6 (2H, m), 1.8–2.0 (2H, m), 3.29 (3H, t, J=7.4), 3.71 (3H, s), 3.87 (6H, s), 7.13 (2H, s), 7.46 (1H, d, J=16.3), 7.81 (1H, d, J=16.3), 8.41 (1H, s), 13.5–14.0 (1H, brs).

Compound of Example 32

¹H-NMR(DMSO-d₆) δ: 0.94 (3H, t, J=7.2), 1.4–1.5 (2H, m), 1.8–2.0 (2H, m), 3.0–3.4 (6H, m), 3.61 (3H, s), 3.73 (6H, s), 6.61 (2H, s), 8.39 (1H, s).

Compound of Example 33

¹H-NMR(CDCl₃) δ: 1.02 (3H, t, J=7.2), 1.5–1.6 (2H, m), 2.0–2.1 (2H, m), 3.44 (2H, t, J=7.4), 5.78 (2H, s), 7.3–7.4 (3H, m), 7.5–7.6 (5H, m), 8.04 (1H, s), 8.3–8.4 (2H, m).

Compound of Example 34

¹H-NMR(DMSO-d₆) δ: 0.91 (3H, t, J=6.9), 1.3–1.5 (4H, m), 1.9–2.0 (2H, m), 3.36 (2H, t, J=7.4), 7.5–7.6 (3H, m), 8.2–8.3 (2H, m), 8.43 (1H, s).

Compound of Example 35

¹H-NMR(DMSO-d₆) δ: 2.49 (3H, s), 7.4–7.6 (5H, m), 8.2–8.4 (4H, m), 8.54 (1H, s).

Compound of Example 36

¹H-NMR(DMSO-d₆) δ: 0.88 (3H, t, J=7.2), 1.2–1.6 (6H, m), 1.9–2.0 (2H, m), 3.36 (2H, t, J=7.7), 7.4–7.7 (3H, m), 8.2–8.3 (2H, m), 8.43 (1H, s), 13.6–14.1 (1H, brs).

Compound of Example 37

¹H-NMR(DMSO-d₆) δ: 0.86 (3H, t, J=6.9), 1.2–1.5 (1H, m), 1.8–2.0 (2H, m), 3.34 (2H, t, J=7.9), 7.5–7.6 (3H, m), 8.2–8.3 (2H, m), 8.43 (1H, s).

Compound of Example 38

¹H-NMR(DMSO-d₆) δ: 0.98 (3H, t, J=7.4), 1.4–1.6 (2H, m), 1.9–2.0 (2H, m), 3.36 (2H, t, J=7.7), 7.41 (2H, t, J=8.9), 8.31 (2H, dd, J=6.4, 8.9), 8.43 (1H, s).

Compound of Example 39

¹H-NMR(DMSO-d₆) δ: 0.98 (3H, t, J=7.4), 1.4–1.6 (2H, m), 1.9–2.0 (2H, m), 3.35 (2H, t, J=7.4), 7.78 (2H, d, J=8.4), 8.21 (2H, d, J=8.4), 8.43 (1H, s).

Compound of Example 40

¹H-NMR(DMSO-d₆) δ: 1.04 (3H, t, J=7.2), 1.4–1.6 (2H, m), 1.9–2.1 (2H, m), 3.39 (2H, t, J=7.2), 5.70 (2H, s), 6.76 (2H, d, J=8.7), 8.02 (2H, d, J=8.7), 8.44 (1H, s).

Examples 41 to 73

In the same manner as in Example 1, except for using any one of the respective compounds obtained in Reference Examples 1 to 5 described above and a predetermined acyl hydrazine derivative, the respective compounds having the structures and melting points shown in Tables 13 to 15 were prepared.

In Tables 13 to 15, Me denotes a methyl group, Et denotes an ethyl group, n-Pr denotes a n-propyl group, i-Pr denotes an isopropyl group, n-Bu denotes a n-butyl group, t-Bu denotes a t-butyl group, n-Pe denotes a n-pentyl group, Ph denotes a phenyl group and Bn denotes a benzyl group, respectively.

TABLE 13

| Example No. | A | R¹ | R² | Melting point (° C.) |
|---|---|---|---|---|
| 41 | Bn–N=CH–N< | n-Bu | Ph | 157–160 |
| 42 | HN–N=CH–N< | n-Bu | –C₆H₄–N(Me)₂ (para) | 236–240 |
| 43 | N=CH–N(Me)–N< | n-Bu | Ph | 193–195 |
| 44 | Me–N=CH–N< | n-Bu | Ph | 213–215 |

TABLE 13-continued

| Example No. | A | R¹ | R² | Melting point (° C.) |
|---|---|---|---|---|
| 45 | HN–CH=N–CH₃ | n-Bu | –C₆H₄–O-n-Pr (4-) | 233–235 |
| 46 | N=CH–N(Et)–CH₃ | n-Bu | Ph | 187–190 |
| 47 | Et–N(CH₃)–CH=N–CH₃ | n-Bu | Ph | 144–146 |
| 48 | HN–CH=N–CH₃ | n-Bu | –C₆H₄–OEt (4-) | 241–243 |
| 49 | " | n-Bu | –C₆H₄–O-Bn (4-) | 230–233 |
| 50 | " | n-Bu | –C₆H₄–Ph (4-) | 244–246 |
| 51 | " | n-Bu | –C₆H₃(OMe)₂ (3,4-) | 180–182 |

(Continued on Table 14)

TABLE 14

| Example No. | A | R¹ | R² | Melting point (° C.) |
|---|---|---|---|---|
| 52 | n–N(CH₃)–CH=N–CH₃ | n-Bu | –C₆H₃Cl₂ (2,4-) | 208–211 |
| 53 | " | n-Bu | –CH₂–C₆H₃(OMe)₂ (3,4-) | 165–168 |
| 54 | " | n-Bu | –C₆H₄–N(Et)₂ (4-) | 215–217 |
| 55 | " | n-Bu | –C₆H₄–NH–Et (4-) | 247–249 |
| 56 | " | n-Bu | –C₆H₄–O-n-Bu (4-) | 230–232 |

TABLE 14-continued
| Example No. | A | R¹ | R² | Melting point (° C.) |
|---|---|---|---|---|
| 57 | " | n-Bu | 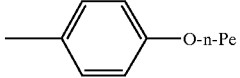 4-(O-n-Pe)-phenyl | 225–228 |
| 58 | " | n-Bu | 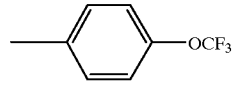 4-OCF₃-phenyl | 273–275 |
| 59 | " | n-Bu | 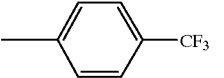 4-CF₃-phenyl | 278–280 |
| 60 | " | n-Bu | 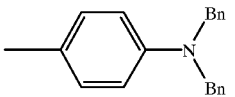 4-N(Bn)₂-phenyl | 134–138 |
| 61 | " | n-Bu | 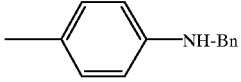 4-NH-Bn-phenyl | 226–229 |
| 62 | " | n-Bu | 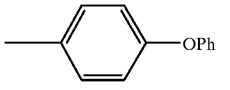 4-OPh-phenyl | 222–225 |
(Continued on Table 15)
TABLE 15
| Example No. | A | R¹ | R² | Melting point (° C.) |
|---|---|---|---|---|
| 63 |  | n-Bu | 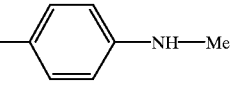 4-NHMe-phenyl | 237–239 |
| 64 | " | n-Bu | 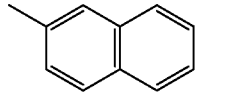 2-naphthyl | 219–222 |
| 65 | " | n-Bu | 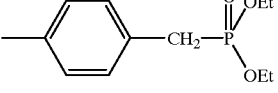 4-(CH₂-P(O)(OEt)₂)-phenyl | 169–171 |
| 66 | " | n-Bu | 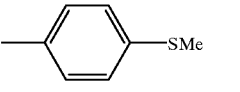 4-SMe-phenyl | 264–265 |
| 67 | " | n-Bu | 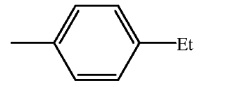 4-Et-phenyl | 248–250 |
| 68 | " | n-Bu | 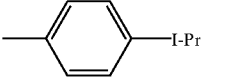 4-i-Pr-phenyl | 228–230 |

TABLE 15-continued

| Example No. | A | R¹ | R² | Melting point (° C.) |
|---|---|---|---|---|
| 69 | " | n-Bu | 4-t-Bu-phenyl | 242–244 |
| 70 | " | n-Bu | 4-(CH₂—OMe)-phenyl | 237–239 |
| 71 | " | n-Bu | 4-(CH₂—O-Bn)-phenyl | 200–203 |
| 72 | " | n-Bu | 2-HO-5-Cl-phenyl | 251–254 |
| 73 | " | n-Bu | 3-hydroxy-2-methylnaphthyl | 266–269 |

The measurement results of NMR of the resulting respective compounds are shown below.

Compound of Example 41

$^1$H-NMR(CDCl$_3$) δ: 1.03 (3H, t, J=7.2), 1.5–1.6 (2H, m), 1.9–2.1 (2H,m), 3.45 (2H, t, J=7.4), 5.49 (2H, s), 7.3–7.4 (5H, m), 7.5–7.6 (3H, m), 7.97 (1H, s), 8.4–8.5 (2H, m).

Compound of Example 42

$^1$H-NMR(DMSO-d$_6$) δ: 1.04 (3H, t, J=7.2), 1.4–1.6 (2H, m), 1.9–2.1 (2H, m), 3.07 (6H, s), 3.40 (2H, t, J=7.4), 6.91 (2H, d, J=8.7), 8.15 (2H, d, J=8.7), 8.45 (1H, s).

Compound of Example 43

$^1$H-NMR(CDCl$_3$) δ: 1.02 (3H, t, J=7.2), 1.5–1.6 (2H, m), 2.0–2.1 (2H, m), 3.44 (2H, t, J=7.4), 4.30 (3H, s), 7.5–7.6 (3H, m), 7.99 (1H, s), 8.3–8.4 (2H, m).

Compound of Example 44

$^1$H-NMR(CDCl$_3$) δ: 1.04 (3H, t, J=7.4), 1.5–1.6 (2H, m), 2.0–2.1 (2H, m), 3.45 (2H, t, J=7.4), 3.97 (3H, s), 7.5–7.6 (3H, m), 7.97 (1H, s), 8.4–8.5 (2H, m).

Compound of Example 45

$^1$H-NMR(DMSO-d$_6$) δ: 0.9–1.1 (6H, m), 1.4–1.6 (2H, m), 1.7–1.8 (2H, m), 1.9–2.0 (2H, m), 3.34 (2H, t, J=7.7), 4.02 (2H, t, J=6.4), 7.11 (2H, d, J=8.4), 8.19 (2H, d, J=8.4), 8.41 (1H, s).

Compound of Example 46

$^1$H-NMR(CDCl$_3$) δ: 1.02 (3H, t, J=7.4), 1.5–1.6 (2H, m), 1.74 (3H, t, J=7.4), 2.0–2.1 (2H, m), 3.44 (2H, t, J=7.7), 4.63 (2H, q, J=7.4), 7.5–7.6 (3H, m), 8.04 (1H, s), 8.3–8.4 (2H, m).

Compound of Example 47

$^1$H-NMR(CDCl$_3$) δ: 1.04 (3H, t, J=7.4), 1.5–1.6 (2H, m), 1.61 (3H, t, J=7.4), 1.9–2.1 (2H, m), 3.44 (2H, t, J=7.4), 4.39 (2H, q, J=7.4), 7.4–7.6 (3H, m), 8.00 (1H, s), 8.4–8.5 (2H, m).

Compound of Example 48

$^1$H-NMR(DMSO-d$_6$) δ: 0.98 (3H, t, J=7.2), 1.38 (3H, t, J=6.9), 1.4–1.6 (2H, m), 1.9–2.0 (2H, m), 3.34 (2H, t, J=7.4), 4.12 (2H, q, J=6.9), 7.09 (2H, d, J=8.7), 8.19 (2H, d, J=8.7), 8.41 (1H, s).

Compound of Example 49

$^1$H-NMR(DMSO-d$_6$) δ: 0.98 (3H, t, J=6.9), 1.4–1.6 (2H, m), 1.8–2.0 (2H, m), 3.34 (2H, t, J=7.4), 5.20 (2H, s), 7.20 (2H, d, J=8.9), 7.3–7.5 (5H, m), 8.21 (2H, d, J=8.9), 8.41 (1H, s).

Compound of Example 50

$^1$H-NMR(DMSO-d$_6$) δ: 0.99 (3H, t, J=7.2), 1.4–1.6 (2H, m), 1.8–2.0 (2H, m), 3.38 (2H, t, J=7.7), 7.3–7.6 (3H, m), 7.78 (2H, d, J=8.2), 7.89 (2H, d, J=7.7), 8.36 (2H, d, J=7.7), 8.43 (1H, s).

Compound of Example 51

$^1$H-NMR(DMSO-d$_6$) δ: 0.98 (3H, t, J=7.2), 1.4–1.6 (2H, m), 1.9–2.0 (2H, m), 3.36 (2H, t, J=6.9), 3.86 (3H, s), 3.90 (3H, s), 7.15 (1H, d, J=8.2), 7.78 (1H, s), 7.86 (1H, d, J=8.2), 8.41 (1H, s).

Compound of Example 52

$^1$H-NMR(DMSO-d$_6$) δ: 0.96 (3H, t, J=7.2), 1.4–1.6 (2H, m), 1.9–2.1 (2H, m), 3.35 (2H, t, J=7.4), 7.65 (1H, dd, J=2.0, 8.4), 7.86 (1H, d, J=2.0), 8.15 (1H, d, J=8.4), 8.45 (1H, s).

Compound of Example 53

$^1$H-NMR(DMSO-d$_6$) δ: 0.95 (3H, t, J=7.4), 1.5–1.6 (2H, m), 1.8–2.0 (2H, m), 3.28 (2H, t, J=7.4), 3.72 (3H, s), 3.73 (3H, s), 4.18 (2H, s), 6.89 (2H, s), 7.01 (1H, s), 8.37 (1H, s).

Compound of Example 54

$^1$H-NMR(DMSO-d$_6$) δ: 0.98 (3H, t, J=7.2), 1.15 (6H, t, J=6.9), 1.4–1.6 (2H, m), 1.9–2.0 (2H, m), 3.33 (2H, t, J=7.4), 3.42 (4H, q, J=6.9), 6.80 (2H, d, J=8.9), 8.06 (2H, d, J=8.9), 8.38 (1H, s).

Compound of Example 55

$^1$H-NMR(DMSO-d$_6$) δ: 0.97 (3H, t, J=6.9), 1.20 (3H, t, J=6.9), 1.4–1.5 (2H, m), 1.8–2.0 (2H, m), 3.0–3.2 (2H, m), 3.32 (2H, t, J=7.9), 6.13 (1H, brs), 6.69 (2H, d, J=7.4), 8.00 (2H, d, J=7.4), 8.38 (1H, s), 13.5–13.9 (1H, brs).

Compound of Example 56

$^1$H-NMR(DMSO-d$_6$) δ: 0.9–1.0 (6H, m), 1.4–1.6 (4H, m), 1.7–1.8 (2H, m), 1.8–2.0 (2H, m), 3.35 (2H, t, J=7.4), 4.07 (2H, t, J=6.4), 7.11 (2H, d, J=8.9), 8.20 (2H, d, J=8.9), 8.40 (1H, s), 13.5–14.0 (1H, brs).

Compound of Example 57

$^1$H-NMR(DMSO-d$_6$) δ: 0.91 (3H, t, J=6.9), 0.98 (3H, t, J=7.4), 1.3–1.6 (6H, m), 1.7–1.8 (2H, m), 1.8–2.0 (2H, m), 3.34 (2H, t, J=7.4), 4.05 (2H, t, J=6.4), 7.10 (2H, d, J=8.9), 8.19 (2H, d, J=8.9), 8.41 (1H, s), 13.5–14.0 (5H, brs).

Compound of Example 58

$^1$H-NMR(DMSO-d$_6$) δ: 0.98 (3H, t, J=71.4), 1.4–1.6 (2H, m), 1.9–2.0 (2H, m), 3.36 (2H, t, J=7.64), 7.58 (2H, d, J=8.6), 8.39 (2H, d, J=8.6), 8.44 (1H, s), 13.6–14.0 (1H, brs).

Compound of Example 59

$^1$H-NMR(DMSO-d$_6$) δ: 0.98 (3H, t, J=7.2), 1.4–1.6 (2H, m), 1.8–2.0 (2H, m), 3.33 (2H, t, J=7.7), 7.92 (2H, d, J=7.9), 8.43 (1H, s), 8.44 (2H, d, J=7.9).

Compound of Example 60

$^1$H-NMR(DMSO-d$_6$) δ: 0.95 (3H, t, J=7.2), 1.3–1.5 (2H, m), 1.8–2.0 (2H, m), 3.30 (2H, t, J=7.7), 4.80 (4H, s), 6.85 (2H, d, J=8.4), 7.2–7.4 (10H, m), 8.00 (2H, d, J=8.4), 8.37 (1H, s).

Compound of Example 61

$^1$H-NMR(DMSO-d$_6$) δ: 0.97 (3H, t, J=7.2), 1.3–1.5 (2H, m), 1.8–2.0 (2H, m), 3.31 (2H, t, J=7.4), 4.37 (2H, d, J=5.9), 6.74 (2H, d, J=8.7), 6.82 (1H, t, J=5.9), 7.2–7.4 (5H, m), 7.98 (2H, d, J=8.7), 8.38 (1H, s), 13.5–14.0 (1H, br s).

Compound of Example 62

$^1$H-NMR(DMSO-d$_6$) δ: 0.97 (3H, t, J=7.2), 1.4–1.6 (2H, m), 1.8–2.0 (2H, m), 3.35 (2H, t, J=7.4), 7.0–7.3 (5H, m), 7.46 (2H, t, J=7.4), 8.27 (2H, d, J=7.7), 8.42 (1H, s).

Compound of Example 63

$^1$H-NMR(DMSO-d$_6$) δ: 0.97 (3H, t, J=7.4), 1.4–1.6 (2H, m), 1.8–2.0 (2H, m), 2.76 (3H, d, J=5.0), 3.32 (2H, t, J=7.4), 6.22 (1H, d, J=5.0), 6.68 (2H, d, J=8.4), 8.02 (2H, d, J=8.4), 8.38 (1H, s), 13.5–14.0 (1H, brs).

Compound of Example 64

$^1$H-NMR(DMSO-d$_6$) δ: 1.00 (3H, t, J=7.2), 1.4–1.6 (2H, m), 1.9–2.0 (2H, m), 3.40 (2H, t, J=7.7), 7.5–7.7 (2H, m), 8.0–8.1 (1H, m), 8.10 (1H, d, J=8.4), 8.1–8.2 (1H, m), 8.37 (1H, d, J=8.4), 8.44 (1H, s), 8.88 (1H, s).

Compound of Example 65

$^1$H-NMR(DMSO-d$_6$) δ: 0.98 (3H, t, J=7.2), 1.1–1.2 (6H, m), 1.4–1.6 (2H, m), 1.9–2.0 (2H, m), 3.2–3.4 (4H, m), 3.9–4.1 (4H, m), 7.48 (2H, d, J=7.9), 8.22 (2H, d, J=7.9), 8.43 (1H, s), 13.6–14.0 (1H, brs).

Compound of Example 66

$^1$H-NMR(DMSO-d$_6$) δ: 0.98 (3H, t, J=7.2), 1.4–1.6 (2H, m), 1.9–2.0 (2H, m), 2.56 (3H, s), 3.35 (2H, t, J=7.4), 7.44 (2H, d, J=8.7), 8.19 (2H, d, J=8.7), 8.41 (1H, s).

Compound of Example 67

$^1$H-NMR(DMSO-d$_6$) δ: 0.98 (3H, t, J=7.2), 1.24 (3H, t, J=7.4), 1.4–1.6 (2H, m), 1.9–2.0 (2H, m), 2.70 (2H, q, J=7.4), 3.35 (2H, t, J=7.9), 7.41 (2H, d, J=7.9), 8.19 (2H, d, J=7.9), 8.42 (1H, s).

Compound of Example 68

$^1$H-NMR(DMSO-d$_6$) δ: 0.98 (3H, t, J=7.4), 1.26 (6H, d, J=6.9), 1.4–1.6 (2H, m), 1.9–2.0 (2H, m), 2.99 (1H, quint., J=6.9), 3.36 (2H, t, J=7.4), 7.44 (2H, d, J=7.9), 8.20 (2H, d, J=7.9), 8.42 (1H, s).

Compound of Example 69

$^1$H-NMR(DMSO-d$_6$) δ: 0.98 (3H, t, J=7.2), 1.35 (9H, s), 1.4–1.5 (2H, m), 1.9–2.0 (2H, m), 3.36 (2H, t, J=7.7), 7.60 (2H, d, J=8.2), 8.21 (2H, d, J=8.2), 8.42 (1H, s).

Compound of Example 70

$^1$H-NMR(DMSO-d$_6$) δ: 0.98 (3H, t, J=6.9), 1.4–1.6 (2H, m), 1.9–2.0 (2H, m), 3.35 (2H, t, J=6.9), 3.36 (3H, s), 4.51 (2H, s), 7.50 (2H, d, J=8.4), 8.25 (2H, d, J=8.4), 8.42 (1H, s).

Compound of Example 71

$^1$H-NMR (DMSO-d$_6$) δ: 0.98 (3H, t, J=7.2), 1.4–1.6 (2H, m), 1.9–2.0 (2H, m), 3.38 (2H, t, J=7.7), 4.60 (2H, s), 4.64 (2H, s), 7.2–7.4 (5H, m), 7.56 (2H, d, J=8.2), 8.28 (2H, d, J=8.2), 8.42 (1H, s), 13.6–14.0 (1H, brs).

Compound of Example 72

$^1$H-NMR(DMSO-d$_6$) δ: 0.98 (3H, t, J=7.2), 1.4–1.6 (2H, m), 1.9–2.0 (2H, m), 3.36 (2H, t, J=8.2), 7.11 (1H, dd, J=2.0, 8.4), 7.16 (1H, d, J=2.0), 8.16 (1H, d, J=8.4), 8.49 (1H, s), 11.49 (1H, brs).

Compound of Example 73

$^1$H-NMR(DMSO-d$_6$) δ: 1.00 (3H, t, J=7.2), 1.4–1.6 (2H, m), 1.9–2.0 (2H, m), 3.42 (2H, t, J=7.7), 7.3–7.6 (3H, m), 7.79 (1H, d, J=7.9), 8.03 (1H, d, J=8.7), 8.50 (1H, s), 8.83 (1H, s), 11.14 (1H, brs), 13.7–14.1 (1H, brs).

Experiment

Adenosine A3 Receptor Binding Capacity Test of Triazolopurine Derivative (1)

According to the method described in Molecular Pharmacology, 45, 978 (1994), an adenosine A3 receptor binding capacity test was performed.

A cell membrane of human renal endothelial cells HEK-293 transformed with plasmid coding an adenosine A3 receptor was isolated in a Tris-hydrochloric acid buffer (pH 7.7) in accordance with a conventional method, and then the cell membrane was treated with N$^6$-(4-aminobenzyl)-9-[5-(methylcarbonyl)-β-D-ribofuranosyl]adenine (AB-MECA) labelled with $^{125}$I to prepare a cell membrane bound with the compound.

Then, this cell membrane and a test compound were incubated and the amount of [$^{125}$I]AB-MECA liberated was measured. The concentration of the test compound when 50% of [$^{125}$I]AB-MECA is liberated, IC$_{50}$, was determined from the measured value of the test compound at each concentration.

The adenosine A1 receptor binding capacity and adenosine A2 receptor binding capacity of the test compound were measured according to the method described in Archives of Pharmacology, 336, 204 (1987) and The Journal of Pharmacology and Experimental Therapeutics, 251 (3), 888 (1989) and then evaluated as IC$_{50}$.

The measurement results are shown in the following tables.

TABLE 16

| Example No. | Receptor binding capacity (IC$_{50}$) (nM) | | |
|---|---|---|---|
| | Adenosine A1 | Adenosine A2 | Adenosine A3 |
| 1 | 101 | 551 | 2.1 |
| 2 | N. D. | N. D. | 96 |
| 3 | 2.6 × 10$^3$ | 3 × 10$^3$ | 95 |
| 4 | 22 | 71 | <1 |
| 5 | — | 184 | <1 |
| 6 | 178 | 247 | <1 |
| 7 | — | 58 | 1.8 |
| 9 | — | 18 | <1 |
| 12 | 1 × 10$^3$ | 2.5 × 10$^3$ | <1 |
| 13 | 228 | 899 | 1.2 |
| 15 | 42 | 208 | <1 |
| 17 | 1.3 × 10$^3$ | 723 | 1.1 |
| 18 | 6.4 | 23 | <1 |
| 19 | 93 | 546 | 1.5 |
| 20 | 21 | 31 | 7.4 |
| 21 | — | 2.6 × 10$^3$ | <1 |
| 22 | — | 361 | <1 |
| 23 | — | 115 | <1 |
| 25 | — | 56 | 1.1 |
| 26 | — | 67 | <1 |
| 27 | — | 1.6 × 10$^3$ | <1 |
| 28 | — | 188 | <1 |
| 34 | — | 205 | <1 |
| 35 | — | 111 | <1 |

TABLE 17

| Example No. | Receptor binding capacity (IC$_{50}$) (nM) | | |
|---|---|---|---|
| | Adenosine A1 | Adenosine A2 | Adenosine A3 |
| 36 | — | 7.8 × 10$^3$ | 2.2 |
| 37 | — | 3.7 × 10$^3$ | 9.0 |
| 42 | — | >1 × 10$^4$ | <1 |
| 45 | — | >1 × 10$^4$ | <1 |
| 48 | — | 3.8 × 10$^3$ | <1 |
| 49 | — | >1 × 10$^4$ | 1.7 |
| 50 | — | >1 × 10$^4$ | 5.0 |
| 51 | — | >1 × 10$^4$ | 1.6 |
| 54 | — | >1 × 10$^4$ | 7.8 |
| 58 | — | >1 × 10$^4$ | 5.8 |
| 59 | — | >1 × 10$^4$ | <1 |
| 60 | — | >1 × 10$^4$ | 15 |
| 61 | — | 1.8 × 10$^3$ | <1 |
| 62 | — | >1 × 10$^4$ | 6.6 |
| 63 | — | 2.4 × 10$^3$ | 1.0 |
| 64 | — | 716 | <1 |
| 65 | — | >1 × 10$^4$ | 3.7 |
| 66 | — | >1 × 10$^4$ | 3.3 |
| 67 | — | 1.8 × 10$^3$ | 5.4 |
| 68 | — | >1 × 10$^4$ | 5.1 |
| 69 | — | >1 × 10$^4$ | 1.2 |

As is apparent from the tables, the compounds of the preset invention have the affinity to the adenosine A3 receptor and its selectivity is high.

Preparation Example 1
(Preparation of tablets)

Two-thousands tablets, each of which contains 300 mg of the compound (5-methyl-8-phenyl-1H-1,2,4-triazolo[5,1-i]purine) obtained in Example 1 as an active ingredient, were prepared according to the following formulation.

| Compound obtained in Example 1 | 600 g |
|---|---|
| Lactose (Japanese Pharmacopoeia) | 67 g |
| Cornstarch (Japanese Pharmacopoeia) | 33 g |
| Calcium carboxymethylcellulose (Japanese Pharmacopoeia) | 25 g |
| Methylcellulose (Japanese Pharmacopoeia) | 12 g |
| Magnesium stearate (Japanese Pharmacopoeia) | 3 g |

According to the formulation described above, desired tablets were obtained by sufficiently mixing the compound obtained in Example 1, lactose, cornstarch and calcium carboxymethylcellulose, granulating the resulting mixture using an aqueous methylcellulose, passing the granules through a #24 mesh sieve, admixing the granules with magnesium stearate and compressing the admixture into tablets.

Preparation Example 2
(Preparation of capsules)

Two-thousands hard gelatin capsules, each of which contains 200 mg of the compound (5-n-butyl-8-(3,4,5-trimethoxyphenyl)-1H-1,2,4-triazolo[5,1-i]purine) obtained in Example 12 as an active ingredient, were prepared according to the following formulation.

| Compound obtained in Example 12 | 400 g |
|---|---|
| Crystalline cellulose (Japanese Pharmacopoeia) | 60 g |
| Cornstarch (Japanese Pharmacopoeia) | 34 g |
| Talc (Japanese Pharmacopoeia) | 4 g |
| Magnesium stearate (Japanese Pharmacopoeia) | 2 g |

According to the formulation described above, desired capsules were obtained by pulverizing the respective ingredients to form powders, mixing the powders to obtain an uniform mixture and filling a gelatin capsule for oral administration having a desired size with the mixture.

What is claimed is:

1. A triazolopurine derivative represented by the general formula (1):

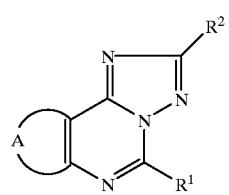

(1)

wherein R$^1$ represents an alkyl group, or a phenyl group which is optionally substituted with a lower alkyl group; R$^2$ represents a pyridyl group, a furyl group, a thienyl group, a lower alkyl group, a phenyl lower alkyl group which optionally has 1 to 3 lower alkoxy groups as a substituent, a styryl group which optionally has 1 to 3 lower alkoxy groups as a substituent, a naphthyl group which optionally has a hydroxy group as a substituent, or a phenyl group which optionally has 1 to 3 groups selected from lower alkyl group, lower alkoxy group, nitro group, hydroxyl group, amino group, N-lower alkylamino group, N,N-di lower alkylamino group, N-phenyl lower alkylamino group, N,N-bisphenyl lower alkylamino group, phenyl group, phenoxy group, phenyl lower alkoxy group, halogen-substituted lower alkyl group, halogen-substituted lower alkoxy group, di lower alkylphosphorylmethyl group, lower alkylthio group, lower alkoxy lower alkyl group, phenyl lower alkoxy lower alkyl group and halogen atom as a substituent; and A represents a group:

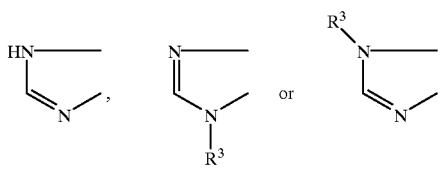

wherein $R^3$ represents a lower alkyl group or a phenyl lower alkyl group.

2. The triazolopurine derivative according to claim 1, wherein A is a group:

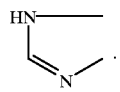

3. The triazolopurine derivative according to claim 2, wherein $R^2$ is a pyridyl group, a furyl group, a styryl group, a naphthyl group which optionally has a hydroxyl group as a substituent, a phenyl group which optionally has a group selected from lower alkyl group, N-lower alkylamino group, N,N-di lower alkylamino group, N-phenyl lower alkylamino group, N,N-bisphenyl lower alkylamino group, phenyl group, phenoxy group, phenyl lower alkoxy group, halogen-substituted lower alkyl group, halogen-substituted lower alkoxy group, di lower alkylphosphorylmethyl group, lower alkylthio group, hydroxyl group and halogen atom as a substituent, a phenyl group substituted with a hydroxyl group and a halogen atom, or a phenyl group having 1 to 3 lower alkoxy groups as a substituent.

4. The triazolopurine derivative according to claim 3, which is selected from the group of the following compounds (a), (b) and (c):

(a) compound wherein $R^1$ is an alkyl group or a lower alkyl-substituted phenyl group and $R^2$ is a phenyl group, (b) compound wherein $R^1$ is a n-butyl group and R is a pyridyl group, a furyl group, a styryl group, a naphthyl group which optionally has ahydroxy group as a substituent, aphenyl group which optionally has a group selected from lower alkyl group, N-lower alkylamino group, N,N-di lower alkylamino group, N-phenyl lower alkylamino group, N,N-bisphenyl lower alkylamino group, phenyl group, phenoxy group, phenyl lower alkoxy group, halogen-substituted lower alkyl group, halogen-substituted lower alkoxy group, di lower alkylphosphorylmethyl group, lower alkylthio group, hydroxyl group and halogen atom as a substituent, a phenyl group substituted with a hydroxyl group and a halogen atom, or a phenyl group having 1 to 3 lower alkoxy groups as a substituent, and (c) compound wherein $R^1$ is a phenyl group and $R^2$ is a phenyl group having 3 lower alkoxy groups.

5. The triazolopurine derivative according to claim 4, which is selected from the group of the following compounds (i) and (ii):

(i) compound wherein $R^1$ is a lower alkyl group and $R^2$ is a phenyl group, and (ii) compound wherein $R^1$ is a n-butyl group and $R^2$ is a naphthyl group which optionally has a hydroxy group as a substituent, a phenyl group which optionally has a group selected from lower alkyl group, N,N-di lower alkylamino group, N-phenyl lower alkylamino group, phenyl group, phenoxy group, phenyl lower alkoxy group, halogen-substituted lower alkyl group, halogen-substituted lower alkoxy group, di lower alkylphosphorylmethyl group, lower alkylthio group and halogen atom as a substituent, a phenyl group substituted with a hydroxyl group and a halogen atom, or a phenyl group having 1 to 3 lower alkoxy groups as a substituent.

6. The triazolopurine derivative according to claim 5, which is selected from the group consisting of:

5-n-butyl-8(3,4,5-trimethoxyphenyl)-1H-1,2,4-triazolo[5,1-i]purine, 5-n-butyl-8-(4-chlorophenyl)-1H-1,2,4-triazolo[5,1-i]purine, 5-n-butyl-8-(4-methoxyphenyl)-1H-1,2,4-triazolo[5,1-i]purine, 5-n-butyl-8-[4-(N,N-dimethylamino)phenyl]-1H-1,2,4-triazolo[5,1-i]purine, 5-n-butyl-8-(4-propoxyphenyl)-1H-1,2,4-triazolo[5,1-i]purine, 5-n-butyl-8-(4-ethoxyphenyl)-1H-1,2,4-triazolo[5,1-i]purine, 8-(4-biphenylyl)-5-n-butyl-1H-1,2,4-triazolo[5,1-i]purine, 5-n-butyl-8-(4-trifluoromethylphenyl)-1H-1,2,4-triazolo[5,1-i]purine, and 5-n-pentyl-8-phenyl-1H-1,2,4-triazolo[5,1-i]purine.

7. The triazolopurine derivative according to claim 6, which is selected from the group consisting of:

5-n-butyl-8-(4-methoxyphenyl)-1H-1,2,4-triazolo[5,1-i]purine, 5-n-butyl-8-(3,4,5-trimethoxyphenyl)-1H-1,2,4-triazolo[5,1-i]purine, and 8-(4-biphenylyl)-5-n-butyl-1H-1,2,4-triazolo[5,1-i]purine.

8. A pharmaceutical composition comprising the triazolopurine derivative of any one of claims 1 to 7 and a pharmaceutically acceptable carrier.

9. A method for treatment of asthma comprising administering, to a subject in need of such treatment, a pharmaceutically effective amount of a triazolopurine derivative of any one of claims 1 to 7.

10. A method of blocking or stimulating an adenosine A3 receptor, which comprises administering an active amount of the triazolopurine derivative of any one of claims 1 to 7.

* * * * *